United States Patent [19]

Fenster et al.

[11] Patent Number: 5,964,707
[45] Date of Patent: Oct. 12, 1999

[54] THREE-DIMENSIONAL IMAGING SYSTEM

[75] Inventors: Aaron Fenster; Shane Dunne; Janpeter T. Larsen, all of London, Canada

[73] Assignee: Life Imaging Systems Inc., Canada

[21] Appl. No.: 09/149,443

[22] Filed: Sep. 9, 1998

Related U.S. Application Data

[63] Continuation of application No. 08/562,590, Nov. 24, 1995, Pat. No. 5,842,473, which is a continuation-in-part of application No. 08/419,049, Apr. 4, 1995, Pat. No. 5,562,095, which is a continuation of application No. 08/158,267, Nov. 29, 1993, abandoned, and a continuation-in-part of application No. PCT/CA95/00375, Jun. 23, 1995, which is a continuation of application No. 08/264,800, Jun. 23, 1994, Pat. No. 5,454,371.

[51] Int. Cl.⁶ .................................................. A61B 8/00
[52] U.S. Cl. ............................................................ 600/443
[58] Field of Search .................................... 600/443, 445, 600/459; 128/916; 345/419

[56] References Cited

U.S. PATENT DOCUMENTS

| | | | |
|---|---|---|---|
| 4,028,934 | 6/1977 | Sollish | 73/67.8 S |
| 4,070,707 | 1/1978 | Barber . | |

(List continued on next page.)

FOREIGN PATENT DOCUMENTS

| | | | |
|---|---|---|---|
| A0109341 | 5/1984 | European Pat. Off. . | |
| A0430506 | 6/1991 | European Pat. Off. . | |
| 0514584 | 11/1992 | European Pat. Off. | A61B 8/00 |
| A2709392 | 3/1995 | France . | |
| 3610439 | 10/1987 | Germany | A61B 8/08 |
| WO9103792 | 3/1991 | WIPO . | |
| WO9400052 | 1/1994 | WIPO . | |

OTHER PUBLICATIONS

Wollschlager, et al., WO 90/13259, Nov. 15, 1990, "Device For Transoesophagal Echocardiography," Abstract.

Chapelon, et al., WO 92/15253, Sep. 17, 1992, "Therapeutic Endo–Rectal Probe, In Particular For Treatment of Prostatic Cancer," Abstract.

Roth, WO 91/03792, Mar. 21, 1991, "System and Method for Transforming Two Dimensional Signals of a Hand Held Sector Transducer Into Three Dimensional Signals," Abstract.

Webler, et al., WO 94/00052, Jan. 6, 1994, "Automated Position Translator For Ultrasonic Imaging Probe," Abstract.

McCann, A., et al., "Multidimensional Ultrasonic Imaging for Cardiology," Proc. IEEE, vol. 76, No. 9, Sep. 1988, New York, USA, pp. 1063–1072.

(List continued on next page.)

*Primary Examiner*—George Manuel
*Attorney, Agent, or Firm*—Fitzpatrick, Cella, Harper & Scinto

[57] ABSTRACT

A three-dimensional ultrasound imaging system includes an ultrasound probe to direct ultrasound waves to and to receive reflected ultrasound waves from a target volume of a subject under examination. The ultrasound probe is swept over the target volume along a linear scanning path and the reflected ultrasound waves are conveyed to a computer wherein successive two-dimensional images of the target volume are digitized. The digitized two-dimensional images can be used to generate a three-dimensional image with virtually no delay. A user interface allows a user to manipulate the displayed image. Specifically, the entire displayed image may be rotated about an arbitrary axis, a surface of the displayed image may be translated to provide different cross-sectional views of the image and a selected surface of the displayed image may be rotated about an arbitrary axis. All of these manipulations can be achieved via a single graphical input device such as a mouse connected to the computer.

1 Claim, 25 Drawing Sheets

U.S. PATENT DOCUMENTS

| | | |
|---|---|---|
| 4,271,706 | 6/1981 | Ledley ........................................ 73/614 |
| 4,341,120 | 7/1982 | Anderson .................................... 73/618 |
| 4,564,018 | 1/1986 | Hutchison et al. ...................... 128/660 |
| 4,747,411 | 5/1988 | Ledley ..................................... 128/660 |
| 4,763,661 | 8/1988 | Sommer et al. . |
| 4,819,650 | 4/1989 | Goldstein ........................... 128/661.01 |
| 4,841,979 | 6/1989 | Dow et al. .............................. 128/660 |
| 4,858,613 | 8/1989 | Fry et al. ............................... 128/660 |
| 4,866,614 | 9/1989 | Tam ................................... 364/413.25 |
| 4,899,318 | 2/1990 | Schlumberger et al. .................... 367/8 |
| 4,932,414 | 6/1990 | Coleman et al. ........................ 128/660 |
| 4,934,370 | 6/1990 | Campbell ........................... 128/661.06 |
| 4,945,478 | 7/1990 | Merickel et al. .................. 364/413.22 |
| 4,955,365 | 9/1990 | Fry et al. .............................. 128/24 A |
| 5,036,855 | 8/1991 | Fry et al. ........................... 128/660.03 |
| 5,072,734 | 12/1991 | Takeuchi ........................... 128/660.05 |
| 5,078,145 | 1/1992 | Furuhata ........................... 128/660.07 |
| 5,081,993 | 1/1992 | Kitney et al. ...................... 128/661.08 |
| 5,152,294 | 10/1992 | Mochizuki et al. ............... 128/662.03 |
| 5,157,931 | 10/1992 | Alsenz . |
| 5,159,931 | 11/1992 | Pini . |
| 5,170,347 | 12/1992 | Tuy et al. ........................... 364/413.22 |
| 5,201,035 | 4/1993 | Stytz et al. .............................. 395/163 |
| 5,282,471 | 2/1994 | Sato . |
| 5,329,929 | 7/1994 | Sato et al. ......................... 128/660.05 |
| 5,454,371 | 10/1995 | Fenster et al. ..................... 128/660.07 |

OTHER PUBLICATIONS

Goddard, J., et al., "3–D Ultrasound Angiograms From Color Flow Mapping Images," Oct. 31, 1991.

Proc. Annual Intl. Conf. IEEE Engineering in Medicine and Biology Soc., vol. 13, Oct. 31, 1991, Orlando, Florda, USA, pp. 146–147.

Halliwell, M., et al., "New Scans from Old: Digital Reformatting of Ultrasound Images," Brit. J. Radiol., vol. 62, No. 741, Sep. 1989, UK, pp. 824–829.

Boissant, J.D. "Shape Reconstruction From Planar Cross Sections," Computer Vision, Graphics, and Image Processing, Oct. 1988, vol. 44, No. 1, ISSN 0734–189X, pp. 1–29.

Picot, P.A., et al., "Three–Dimensional Colour Doppler Imaging of the Carotid Artery," SPIE, vol. 1444, pp. 206–213 (1991).

Rankin, R.N., et al., "Three–Dimensional Sonographic Reconstruction: Techniques and Diagnostic Applilcations," AJR (1993); 161, pp. 695–702 Picot, P.A., et al., "Three–Dimensional Colour Doppler Imaging,".

Ultrasound in Med. & Biol., vol. 19, No. 2, pp. 95–104 (1993).

Tamura, S., et al., "Three–Dimensional Reconstruction of Echocardiograms Based on Orthogonal Sections, " Pattern Recognition, vol. 18, No. 2, ISSN 0031–3203, pp. 115–124.

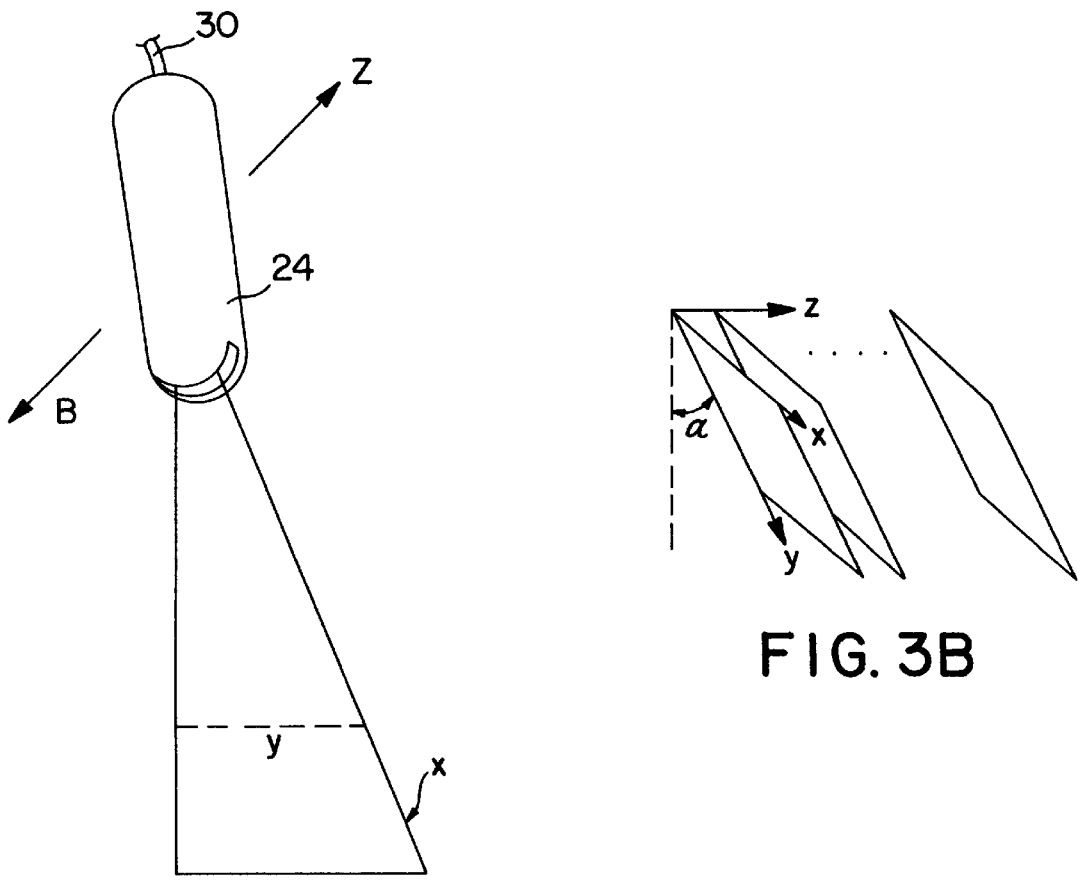
FIG. 3A
FIG. 3B
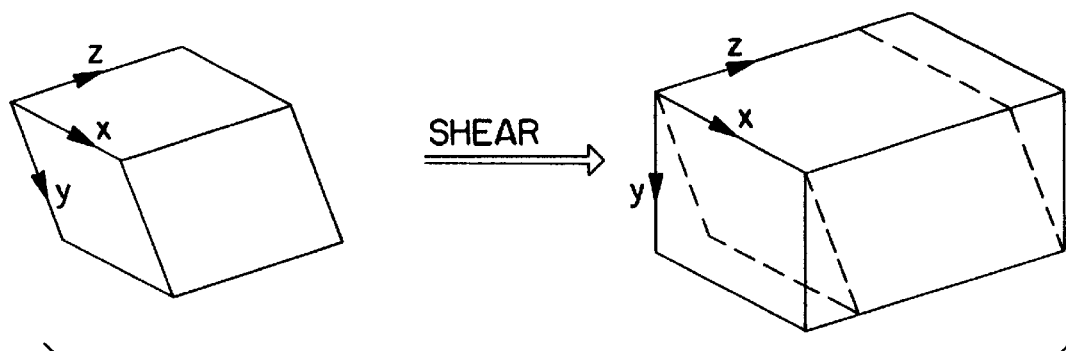
SHEAR
FIG. 3C

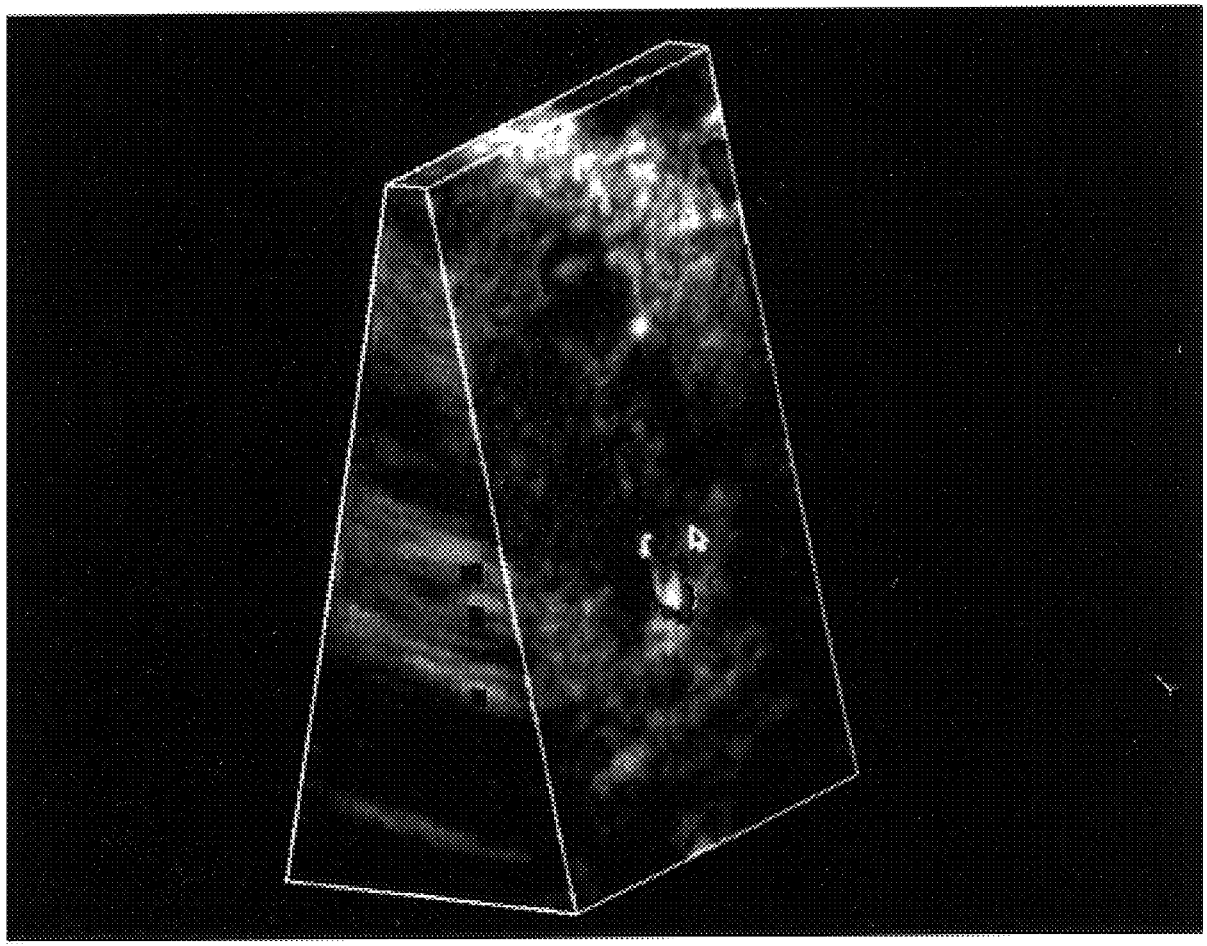
FIG. IOC

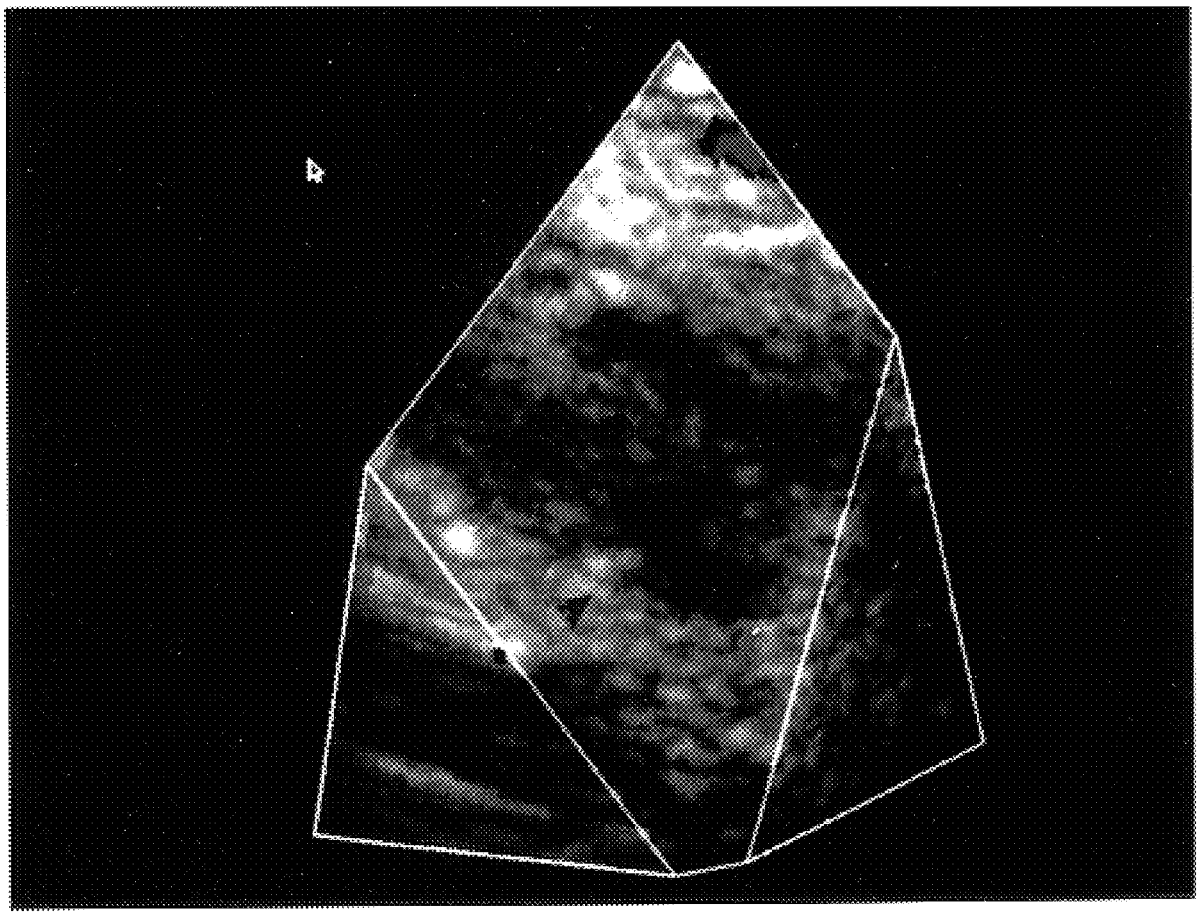
FIG. IIC

THREE-DIMENSIONAL IMAGING SYSTEM

RELATED APPLICATIONS

The present application is a continuation of U.S. Pat. application Ser. No. 08/562,590 filed Nov. 24, 1995, now U.S. Pat. No. 5,842,473,which is a continuation-in-part of U.S. patent application Ser. No. 08/419,049 filed on Apr. 4, 1995, now U.S. Pat. No. 5,562,095, which is a continuation of U.S. patent application Ser. No. 08/158,267 filed on Nov. 29, 1993 now abandoned for an invention entitled "Three-Dimensional Ultrasound Imaging System". The present application is also a continuation-in-part of PCT application serial no. PCT/CA95/00375 filed on Jun. 23, 1995 designating the United States which is a continuation of U.S. patent application Ser. No. 08/264,800 filed Jun. 23, 1994, issued under U.S. Pat. No. 5,454,371 on Oct. 3, 1995 for an invention entitled "Method and System for Constructing and Displaying Three-Dimensional Images".

FIELD OF THE INVENTION

The present invention relates to medical diagnostics and in particular to a method and system for constructing and displaying three-dimensional images.

BACKGROUND OF THE INVENTION

In the medical field, it is common to use ultrasound diagnostic equipment to view internal organs of a subject. For example, in diagnosing prostate cancer, a diagnostician uses transrectal ultrasound (TRUS) to identify whether lesions are present as well as to determine the location, size and extent of lesions if present. Conventional ultrasound diagnostic equipment typically comprise an ultrasound probe for transmitting ultrasound signals into the subject and receiving reflected ultrasound signals therefrom. The reflected ultrasound signals received by the ultrasound probe are processed and a two-dimensional image of the target under examination is formed.

Unfortunately, this conventional equipment produces two-dimensional images even though the target under examination is three-dimensional. Also, the two-dimensional images represent a single thin plane taken at an arbitrary angle to the target making it very difficult to localize the image plane in the target and very difficult to reproduce an image at a particular location at a later time.

In U.S. application Ser. No. 08/419,049 and U.S. Pat. No. 5,454,371, assigned to the assignee of the present application, the contents of which are incorporated herein by reference, three-dimensional ultrasound imaging systems are described. Although, these systems overcome disadvantages associated with the prior art, improvements to enhance imaging and to increase the speed by which three-dimensional images can be generated from two-dimensional ultrasound images are continually being sought.

It is therefore an object of the present invention to provide a novel system and method for generating a three-dimensional image from a succession of two-dimensional images, and a novel ultrasound imaging system.

SUMMARY OF THE INVENTION

According to one aspect of the present invention there is provided a three-dimensional imaging system for acquiring a succession of two-dimensional images of a target volume represented by an array of pixels I(x,y,z) into a three-dimensional image represented by a volumetric image array V(x,y,z) comprising:

scanning means to scan said target volume along a predetermined geometric scanning path and generate a succession of digitized two-dimensional images thereof representing cross-sections of said target volume on a plurality of planes spaced along said scanning path;

memory storing said succession of digitized two-dimensional images together with other related image data defining the location of said two-dimensional images in said memory and defining interpretation information relating to the relative position of pixels within said two-dimensional images and to the relative position of pixels in adjacent two-dimensional images within said target volume;

transformation means receiving said digitized two-dimensional images and said other related image data and transforming said two-dimensional images and said other related image data into a volumetric image array; and display means to generate a three-dimensional image of said target volume from said volumetric image array.

In one embodiment, the geometric scanning path is linear. In this instance, the cross-sections are titled with respect to an axis normal to the linear scanning path. The transformation means transforms the two-dimensional images and the other related image data into the volumetric image array using a shear transformation. The other related image data includes an address pointer indicating the location of the memory of which the two-dimensional image data begins together with data representing the number of pixels along x and y axis of each two-dimensional image. The other related image data also includes physical distance values between adjacent pixels in each of the two-dimensional images as well as the distance between corresponding pixels in adjacent two-dimensional images together with the tilt angle of the cross-sections.

BRIEF DESCRIPTION OF THE DRAWINGS

Embodiments of the present invention will now be described more fully with reference to the accompanying drawings in which:

FIG. 3a is a perspective view of the geometry of the ultrasound probe movement when driven by the ultrasound probe actuating assembly;

FIG. 3b is an illustration of a number of tilted two-dimensional images;

FIG. 3c is an illustration of a shear transformation;

FIGS. 10a to 10c show a three-dimensional image and model in which a plane of the model is translated towards the geometric center of the model;

FIGS. 11a to 11c show a three-dimensional image and model in which a plane of the model is rotated about an axis, angles at about 30° to the horizontal and sloping up and to the right;

DESCRIPTION OF THE PREFERRED EMBODIMENTS

In the applicant's co-pending U.S. patent application Ser. No. 08/419,049 and applicant's U.S. patent issued Ser. No. 5,454,371, three-dimensional ultrasound imaging systems are disclosed. In these systems, when a succession of two-dimensional images have been captured and digitized the two-dimensional images are stored as a stack to form an image data array. Before a three-dimensional image of the scanned target volume can be created, the image data array must be reconstructed to form a volumetric image array. The process of reconstructing the image data array to the volumetric image data array is an unconsuming process which results in significant delays before acquired two-dimensional images can be used to generate a three-dimensional image. The present invention relates to a three-dimensional ultrasound imaging system which overcomes this problem by allowing a three-dimension image to be generated using the two-dimensional image data array without requiring the image data array to undergo reconstruction.

Figure 1:
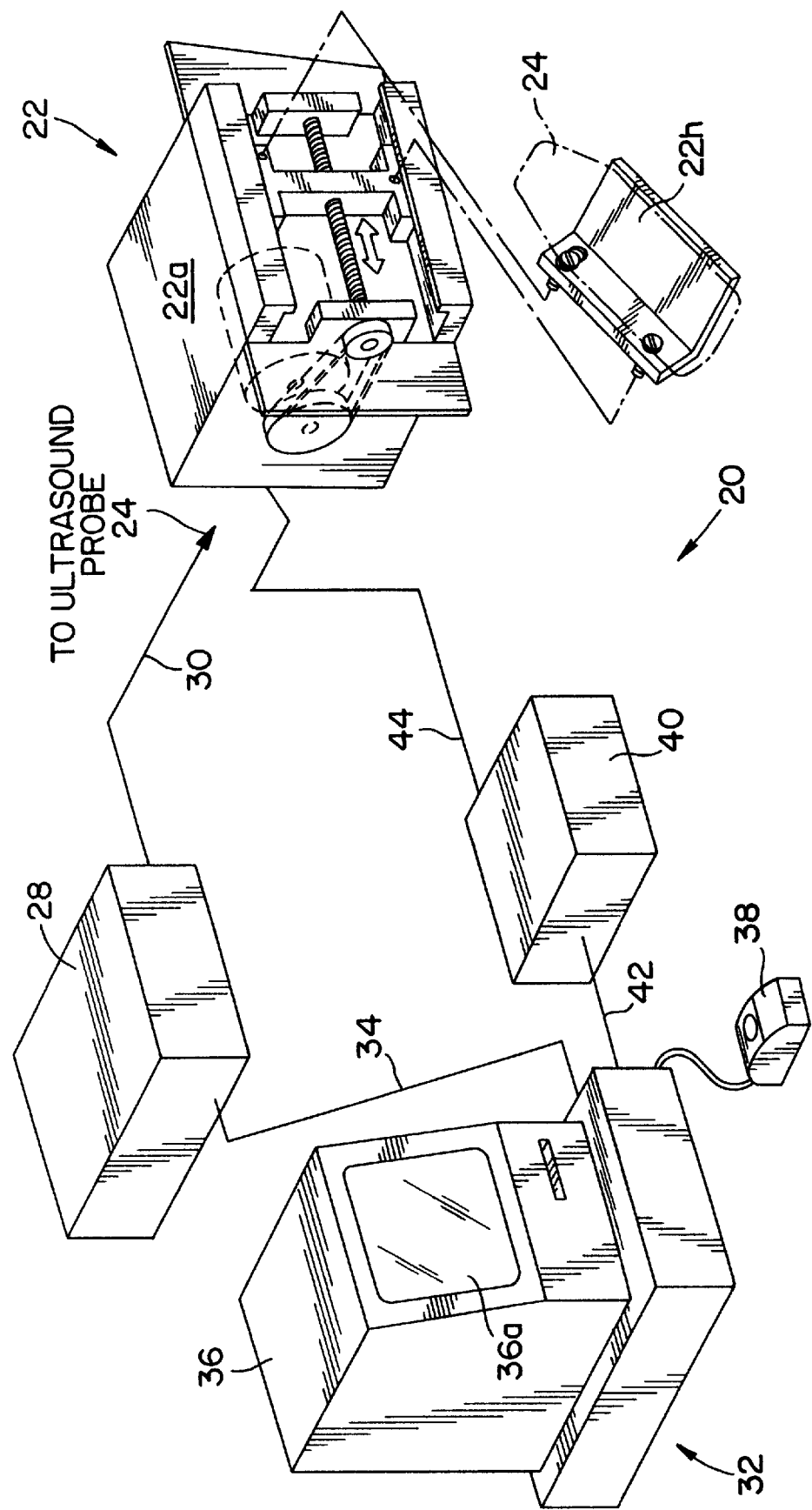
FIG. 1 is a perspective view of a three-dimensional ultrasound imaging system.

Referring now to FIG. 1, a three-dimensional ultrasound imaging system in accordance with the present invention is shown and is generally indicated by reference numeral 20. The system 20 is capable of generating a three-dimensional ultrasound image of a target volume of a subject under examination from a succession of two-dimensional ultrasound images of the target volume and allow the generated three-dimensional image to be manipulated. The subject under examination may be inanimate or animate. In the later case, the system 20 may be used in both medical and veterinary environments and may be used as a diagnostic tool or during surgery to provide updated images of the target volume of the subject undergoing surgery.

The system 20 includes an ultrasound probe actuating assembly 22 for removably retaining an ultrasound probe 24. In this embodiment, the probe actuating assembly 22 is designed to move the ultrasound probe along a linear scanning path Z so that the succession of two-dimensional images of the target volume can be taken.

The ultrasound probe 24 is connected to a clinical ultrasound machine 28 via a communication line 30. The ultrasound machine 28 in turn is connected to a computer 32 via communication line 34. The computer 32 includes a keyboard (not shown), a monitor 36 with a display screen 36a and a graphical input device 38 such as a single button mouse. It should however be realized that many other graphical input devices can be used to allow a user to input commands to the computer. The computer 32 provides output signals to a controller 40 via communication line 42 which in turn provides control signals to the probe actuating assembly 22 via communication line 44 to control the scanning motion of the ultrasound probe 24.

Figure 2:
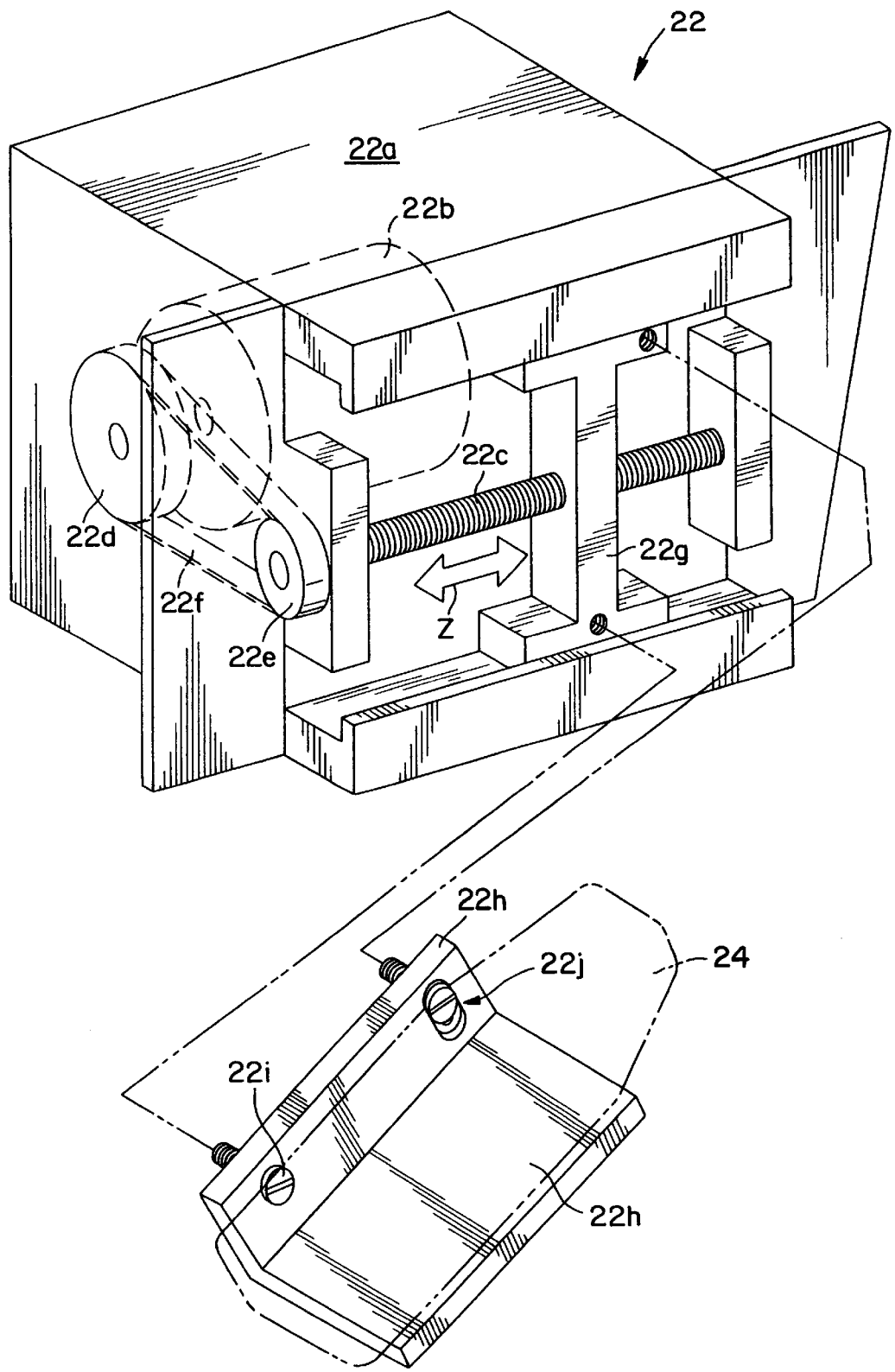
FIG. 2 is a perspective view of an ultrasound probe actuating assembly forming part of the system illustrated in FIG. 1.
Figure 3:
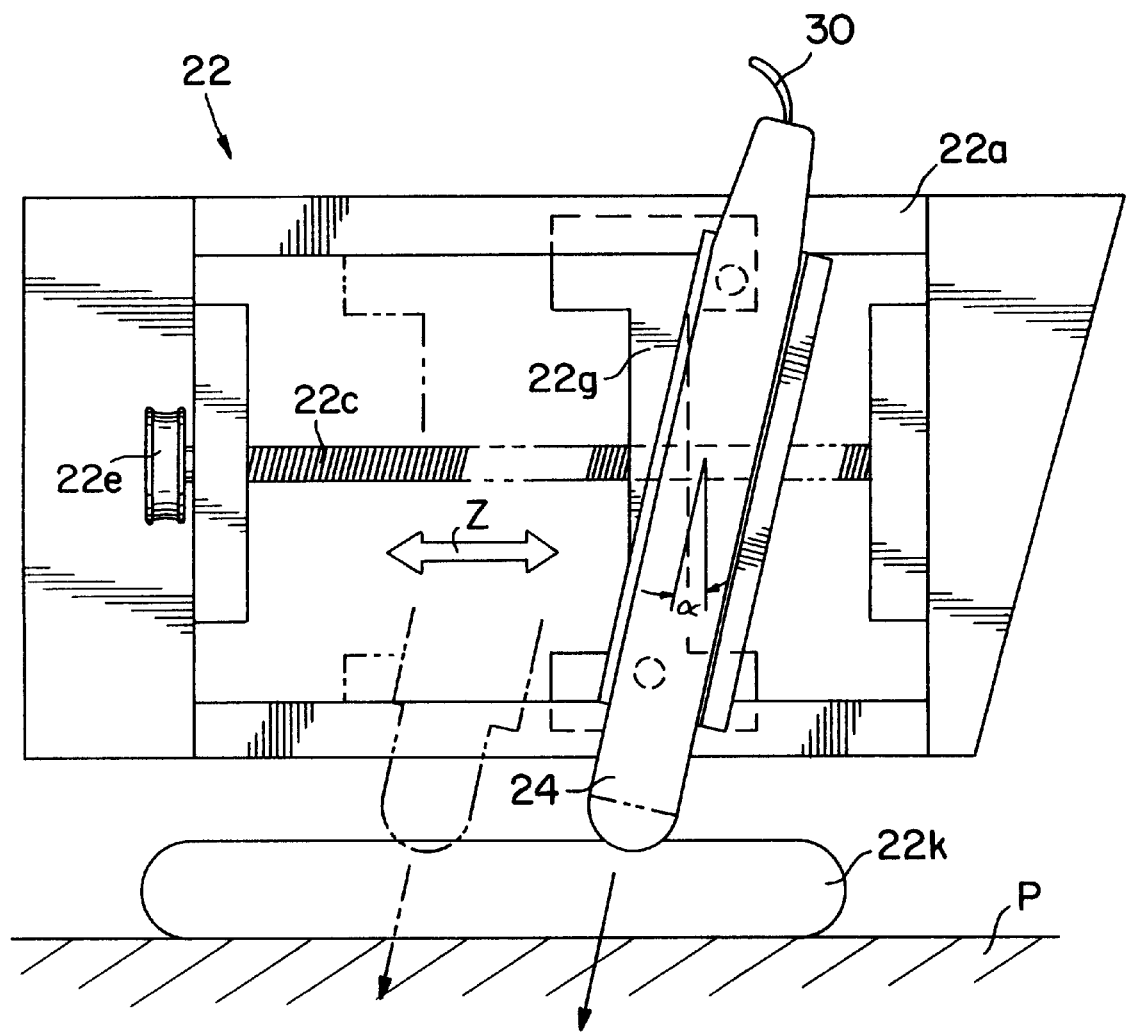
FIG. 3 is a side view of the probe actuating assembly illustrated in FIG. 2 supporting an ultrasound probe.

Referring now to FIGS. 2 and 3, the ultrasound probe 24 and the probe actuating assembly 22 are better illustrated. As can be seen, the probe actuating assembly 22 includes a housing 22a accommodating a motor 22b coupled to a threaded output shaft 22c by way of a pair of reduction wheels 22d and 22e and a belt 22f. An I-block 22g is mounted to the threaded shaft 22e via an internal threaded hole so that the I-block 22g moves along the linear scanning path Z in either direction as represented by arrow B when the threaded shaft 22c is rotated via the motor 22b. A probe holder 22h is secured to the I-block 22g by way of screws 22i and 22j and supports the ultrasound probe 24. The probe holder 22h is positioned relative to the threaded shaft 22c so that the longitudinal axis of the ultrasound probe 24 forms an angle α with an axis normal to the longitudinal axis of the threaded shaft 22c. The angle of inclination of the probe holder 22h can be adjusted by loosening the screws 22i and 22j, rotating the probe holder 22h to the desired position and tightening the screws.

The probe actuating assembly 22 is particularly suited to applications where ultrasound images of a subject's internal organs or lesions such as breast tumours within the trunk of a subject P are to be taken. In these instances, a layer of coupling gel 22k is typically placed on the subject P between the subject and the ultrasound probe 24.

During normal operation, the motor 22b is operated so that it rotates at a constant velocity. Thus, the threaded shaft 22c is rotated at a constant rate causing the probe holder 22h to move the ultrasound probe 24 at a constant rate along the linear scanning path Z. As the ultrasound probe 24 moves along the linear scanning path Z, it transmits ultrasound signals at specific predefined intervals which impinge on the target volume. Reflected ultrasound signals from the target volume are also received by the probe 24 and the converted into analog signals by a crystal (not shown) in the ultrasound probe 24. These analog signals are conveyed to the clinical ultrasound machine 28 where a succession of two-dimensional analog images of the target volume are generated. Each two-dimensional image represents a cross-section of the target volume having x and y dimensions (see FIG. 3a). The operation of the ultrasound probe 24 and clinical ultrasound machine 28 is well known to those of skill in the art and therefore, will not be described in any further detail herein.

Since the velocity of the ultrasound probe 24 moving along the linear scanning path Z and the ultrasound signal transmit intervals of the ultrasound probe 24 are known, the relative position of the two-dimensional analog images of the target volume along the z-axis can be readily determined.

The two-dimensional analog images generated by the ultrasound machine 28 are conveyed to the computer 32 via communication line 34. The computer 32 in turn digitizes the two-dimensional images and stores the digitized image data together with other related image data in a manner which allows a three-dimensional image of the target volume to be displayed virtually without delay as will be described. Once displayed, the computer 32 allows the image to be manipulated as will also be described.

Figure 4:
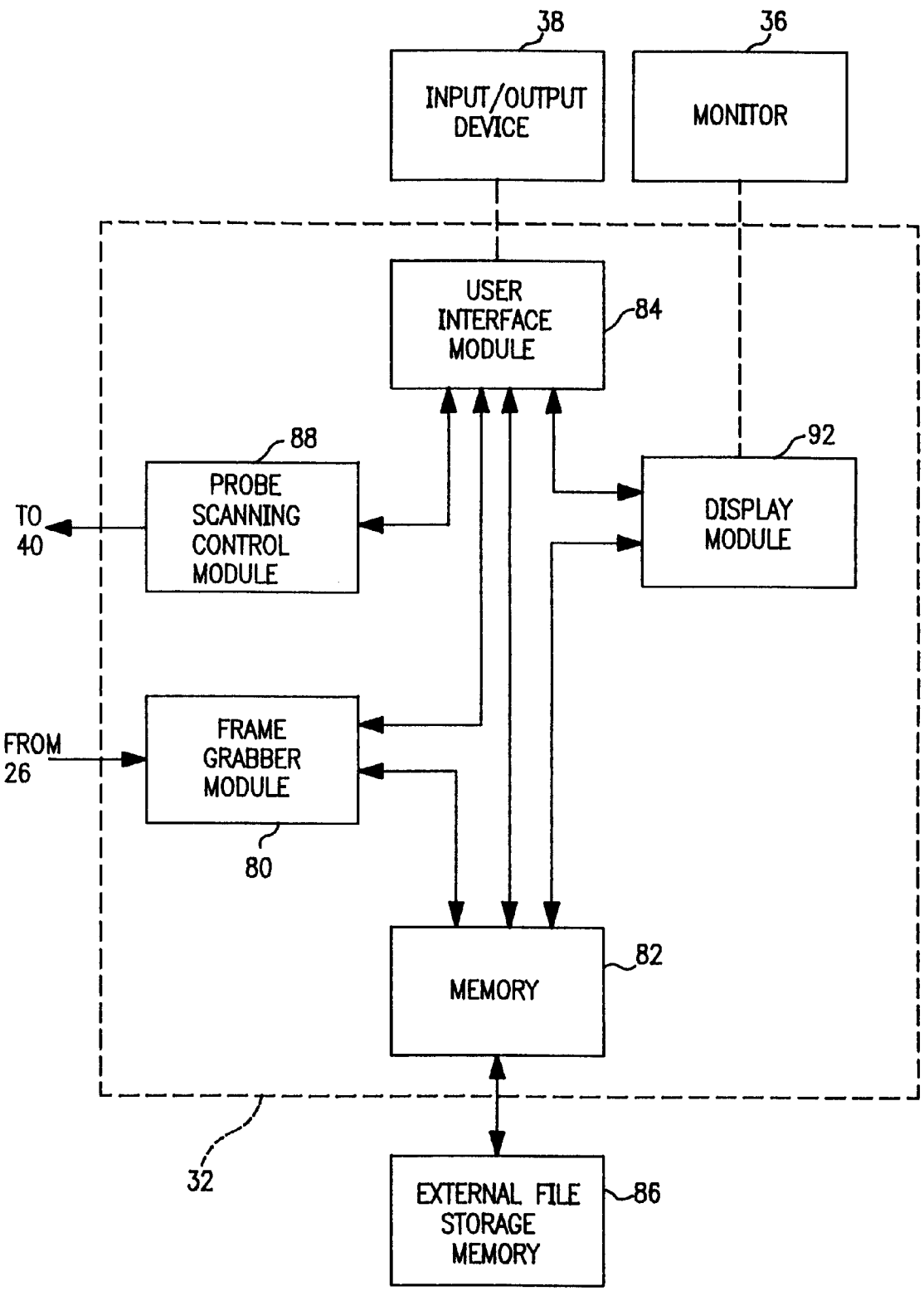
FIG. 4 is a block diagram showing various hardware and software modules of the computer forming part of the system illustrated in FIG. 1.

Referring now to FIG. 4, a block diagram of the computer 32 is shown illustrating some of the hardware and software modules therein. As can be seen, the computer 32 includes a frame grabber module 80, such as for example, an IMAXX Video Capture Board manufactured by Precision Digital Images Corporation of Redmond, Wash., to process the two-dimensional analog images received from the clinical ultrasound machine 28 via communication line 34. Specifically, the frame grabber module 80 captures the digitizes the succession of two-dimensional analog images. Once digitized, the succession of two-dimensional images is stored in local physical memory 82.

The computer 32 also includes a user interface module 84 for interpreting input commands received via the graphical input device 38. As should be realized, the user interface module 84 controls the co-ordinates the operation of the other modules of system 20 in response to input from the graphical input device 38 allowing the user to control the system as desired.

Once a succession of two-dimensional images of the target volume has been captured and digitized by frame grabber module 80 and stored in the physical memory 82, the digitized information can be processed in a number of ways depending on the input commands received by the user interface module 84 from the graphical input device 38. Specifically, the digitized information can be transferred to an external file storage memory 88. The digitized information, whether stored in local physical memory 82 or in the external file storage memory 88, may be processed by a display module 92 in response to input received from graphical input device 38 so that a three-dimensional image of the target volume can be displayed on the screen 36a of the monitor 36 and manipulated as will be described further herein.

The computer 32 also includes a probe scanning control module 98 which provides output signals to controller 40 to actuate the probe actuating assembly 22 and sweep the ultrasound probe 24 along the linear scanning path Z as desired. The probe scanning control module 98 also receives input from the user interface module 84.

Three-Dimensional Imaging

Because the ultrasound probe 24 swept along a linear path Z and since the ultrasound probe 24 is at an angle $\alpha$ relative to an axis normal to the longitudinal axis of the linear scanning path Z, the ultrasound images taken by the ultrasound machine are cross-sections (or image slices) of the target volume on parallel planes tilted by the angle $\alpha$ (see FIG. 3b). Thus, by nature of the acquisition of the ultrasound images, there is a dependency relationship between the y and z co-ordinates which mathematically can be expressed by a shear transformation (see FIG. 3c). Shear transformations, which are well known to those of skill in the art of computer graphics, are linear. The linearity of both the scanning path Z and the shear transformation allows the display module 92 to use the shear transformation as the viewing transformation to convert pixel co-ordinates into corresponding voxel co-ordinates. As such, the display module 92 can act directly on the acquired digitized two-dimensional ultrasound image data and generate a three-dimensional image without requiring the acquired ultrasound image data to undergo the reconstruction processes described in Applicant's U.S. Pat. No. 5,454,371 and patent application Ser. No. 08/419,049. This significantly increases the speed by which a three-dimensional image may be displayed.

In order for the display module 92 to be able to act directly on the acquired digitized ultrasound image data, the display module 92 requires other related image data which includes:

1.) an address pointer defining the address of the location in the physical memory 82 at which the acquired ultrasound image data starts;
2.) the extent of the acquired two-dimensional image data including the number of pixels along the x and y axis of each two-dimensional image as well as the number of two-dimensional images taken in the z-direction;
3.) the physical distance between the centers of adjacent pixels in both the x and y directions in each two-dimensional image as well as the physical distance between corresponding pixels in adjacent two-dimensional images (the z-distance); and
4.) the tilt angle $\alpha$.

The other related image data referred two at points 1 and 2 above defines the location of the acquired digitized ultrasound image data in the memory. This information allows the display module 92 to locate the acquired ultrasound image data and associate sections of the image data with the proper image slices of the target volume. The other related image data referred to at points 3 and 4 above defines image data interpretation information which allows the display module 92 to interpret the acquired ultrasound image data correctly.

Before acquiring two-dimensional images of a target volume using system 20, the other related image data must be defined. Specifically, the frame grabber module 80 is programmed to write the acquired digitized ultrasound image data to the appropriate locations of the physical memory 82 and to generate the address pointer which in turn is stored in a calibration file in physical memory 82. In order to generate the other related image data at step 2, the system 20 is calibrated. Specifically, during calibration, the velocity of the ultrasound probe 24 along the linear scanning path Z and the ultrasound signal transmit interval are determined so that the number of two-dimensional images slices of the target volume to be taken are known. Also, the number of pixels along the x and y axis of the two-dimensional images are measured. The number of pixels in the x and y directions defines the edges of each two-dimensional ultrasound image. Thus, these numbers are used to locate the ultrasound image data within the scanned target volume. Once the numbers are determined they are also stored in the calibration file.

During the system calibration, in order to generate the other related image data at step 3, the center to center distance between two pixels in the same line of an ultrasound image (i.e. in the x direction the determined, the center to center distance between adjacent pixels in two different lines of the ultrasound image are determined (i.e. in the y direction) and the center to center distance between corresponding pixels in two adjacent ultrasound images are determined. During the determination of the distances between the pixels mentioned above, only a few sample measurements between two pixels in the x-direction of an ultrasound image, two pixels in the y-direction of the same ultrasound image are taken and average distances are determined. Since the velocity of the ultrasound probe 24 along the linear scanning path Z is constant and since the ultrasound signal transmit interval is known, the distance between corresponding pixels in adjacent two-dimensional ultrasound images is easily calculated. Once these distances are determined, the distance values are stored in the calibration file. The tilt angle $\alpha$ of the ultrasound probe 24 is also measured and is stored in the calibration file. Once the above other related image data is stored in the calibration file in physical memory 82, the calibration file is stored in the external file storage memory 88. At this stage, the system 20 is ready to acquire two-dimensional image slices of the target volume as will now be described.

Image Capturing

Figure 5A:
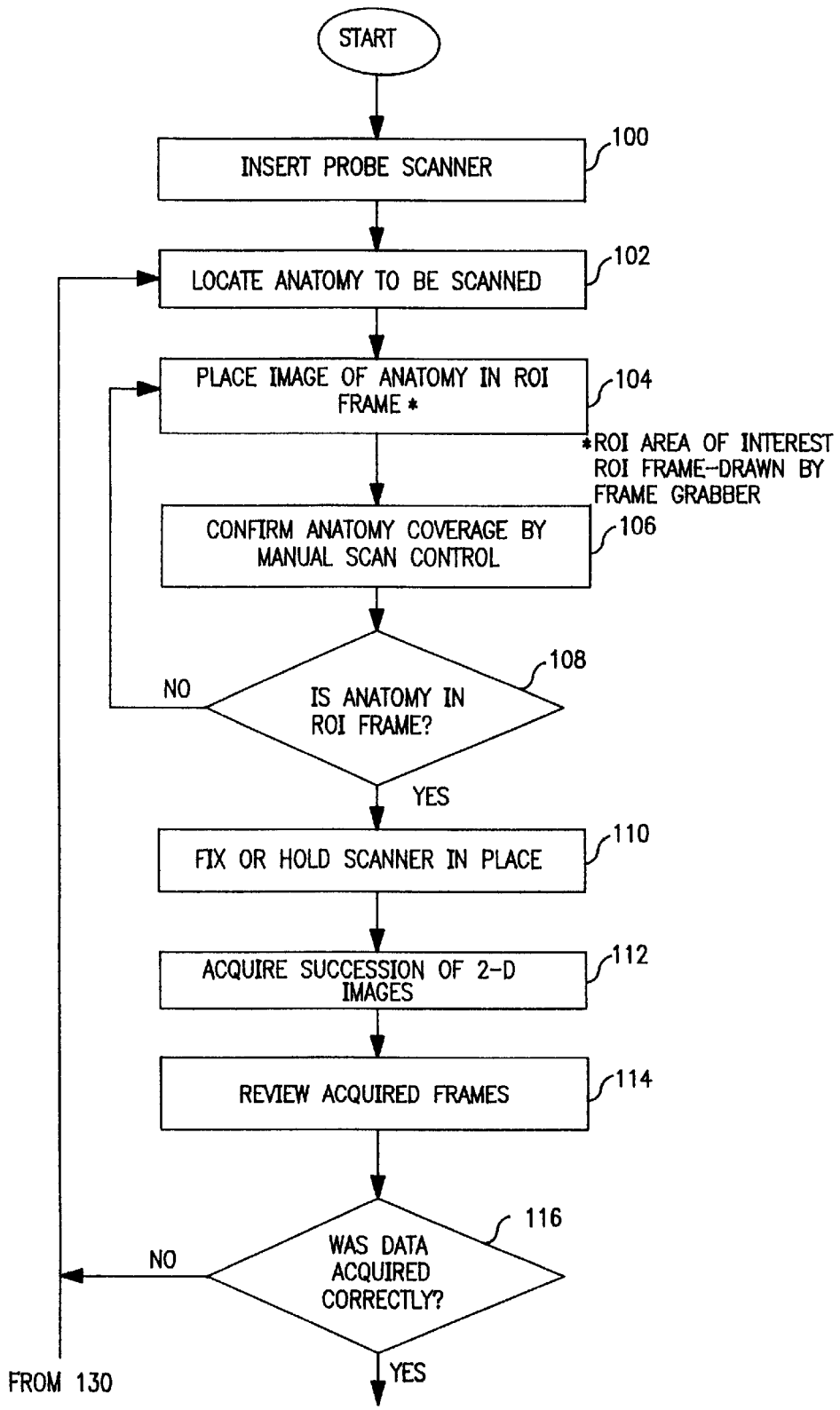
FIG. 5a is a flowchart showing some of the operational steps of the system illustrated in FIG. 1.
Figure 5B:
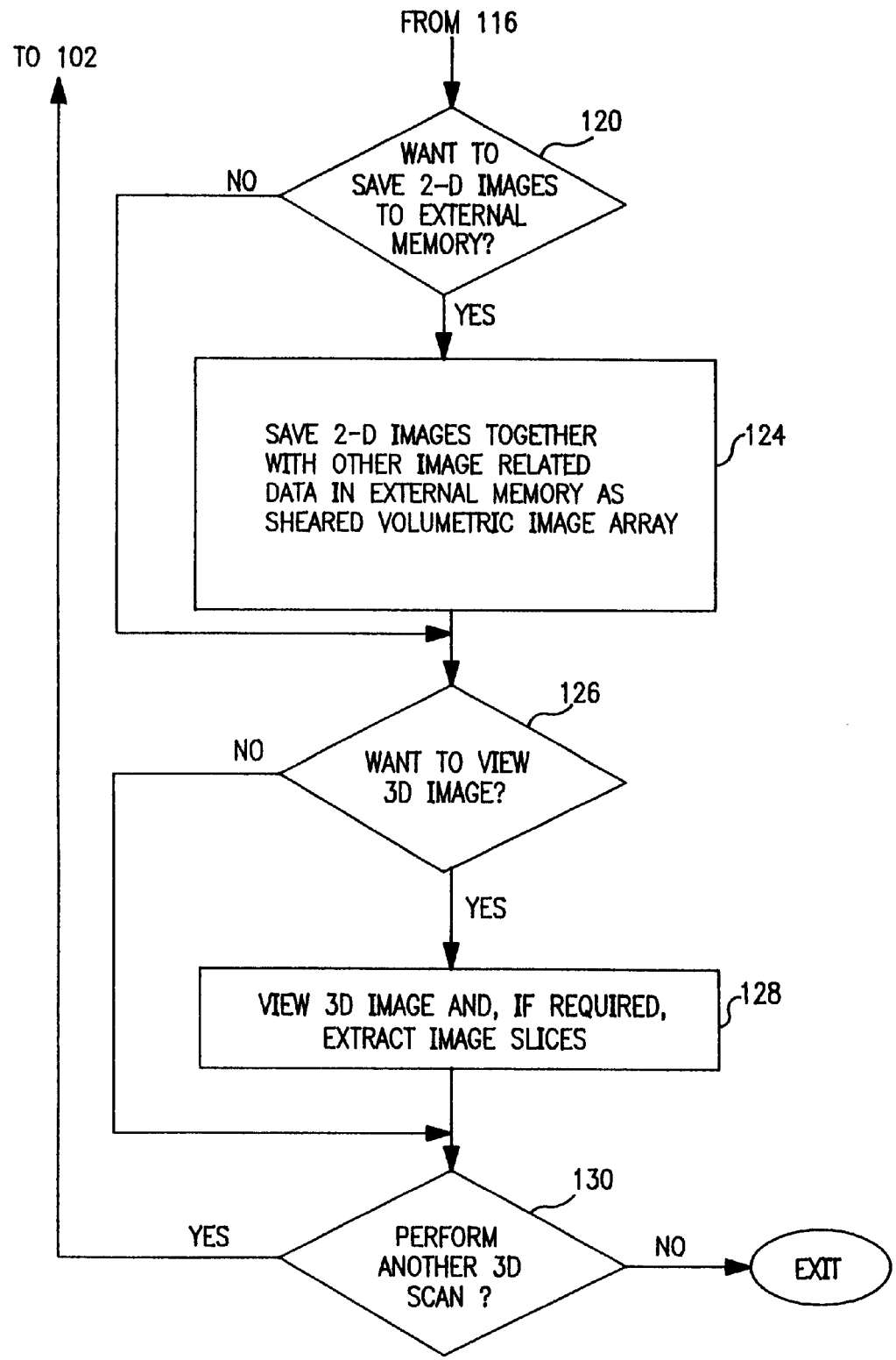
FIG. 5b is a flowchart showing additional operational steps of the system illustrated in FIG. 1.

With reference now to FIGS. 5a and 5b, when it is desired to operate the three-dimensional ultrasound imaging system 20 to acquire two-dimensional images of the target volume, assuming the system 20 has been calibrated and has the other related image data described above stored in the external file storage memory 88, the ultrasound probe 24 and probe actuating assembly 22 must be properly located with respect to the subject so that the ultrasound waves transmitted by the ultrasound probe 24 are directed at the target volume (see block 102).

Initially, the ultrasound probe transmits ultrasound signals to scan a cross-section of the target volume. The reflected ultrasound signals received from the target volume are conveyed to the clinical ultrasound machine 28 wherein a two-dimensional analog image slice of the target volume upon which the ultrasound signals impinged, is created. The two-dimensional analog image is then conveyed to the computer 32 via communication line 34 wherein it is captured and digitized via frame grabber module 80. The digitized two-dimensional image is then stored in the memory 82.

A copy of the digitized two-dimensional image is then conveyed to the user interface module 84 and the frame is drawn on the screen 36a of the monitor 36 (block 104). The user then manually moves the probe 24 along the linear scanning path Z while it is transmitting ultrasound signals so that two-dimensional analog images generated by the clinical ultrasound machine 28 are captured and digitized by the frame grabber module 80. These two-dimensional images are also then drawn on the screen 36a of monitor 36 via user interface module 84 (block 106). Next, the user is prompted to confirm that the ultrasound signals are properly directed at the target volume after having viewed the frames drawn on the screen 36a of the monitor (block 108). If the target volume is outside of the drawn frames, then operation returns to block 104. Otherwise, the user provides input to the user interface module 84 using the graphical input device 38 to signify that the target volume is within the drawn frames.

Once this has been done, with the probe actuating assembly 22 in place (block 110), the system 20 is ready for proper operation. When a user inputs a start command such as for example by using an external foot or hand switch (not shown), by selecting an appropriate icon displayed on the screen 36a using the graphical input device 38 or alternatively by using a voice command, the user interface module 84 signals the probe scanning module 98. Within the context of the present invention, icon refers to any graphical element displayed on the screen 36a which can be selected using graphical input device 38.

At this point in time, the probe scanning module 98 conveys control signals to the probe actuating assembly 22 via controller 40 so that the ultrasound probe 24 is moved along the linear scanning path Z at a constant velocity. While this occurs, the ultrasound probe 24 is conditioned to transmit ultrasound signals at the predefined intervals so that the entire target volume is scanned. As the ultrasound probe receives reflected ultrasound signals, it conveys analog information to the clinical ultrasound machine 28 which in turn generates two-dimensional analog images. In this manner, a succession of two-dimensional analog images of the target volume representing a volume image are generated by the clinical ultrasound machine 28 in response to the output of the ultrasound probe 24 (block 112). The succession of two-dimensional analog images generated by the clinical ultrasound machine 28 are captured and digitized by the frame grabber module 80. The digitized two-dimensional images are then conveyed to the physical memory 82 and stored as a stack to form an array of two-dimensional images I(x,y,z) with the pixels in the array I(x,y,z) representing pixels of the digitized two-dimensional images. Because the computer 32 controls the movement of the probe actuating assembly 22 and the operation of the ultrasound probe 24, the spatial orientation of the individual two-dimensional images relative to the target volume is known.

In the present embodiment, the two-dimensional images are considered to be grayscale images. However, the present invention does not depend on the "color" of the two-dimensional images to function properly. A grayscale pixel is associated with a gray-level having a value between 0 and $(2^n-1)$ inclusively, with n being the number of bits required for storing the gray-levels. The gray-level 0 is usually used as a "background color" and is said to be Black.

Once the two-dimensional images have been acquired and saved in physical memory 82 to form array I(x,y,z), the user interface module 84 generates a prompt to signify that this stage of the image capturing has been completed. At this time, the user may review the acquired frames individually in the manner described previously (block 114). If the two-dimensional images have been acquired incorrectly (block 116), the user can condition the system 20 to return to block 102. If the two-dimensional images have been acquired correctly, the user interface module 84 generates a prompt to determine if the acquired two-dimensional images together with the other related image data in the calibration file are to be saved in the external file storage memory 88 (block 120) together as a sheared volumetric image array V(x,y,z). If the user selects the prompt, the acquired two-dimensional images together with the other related image data are saved as the sheared volumetric image array in the external file storage memory 88 (block 124).

Following this, or if the user does not elect to save the two-dimensional image data to the external memory 88, the user is prompted to decide whether the three-dimensional image is to be displayed on the screen 36a of the monitor 36 (block 126). If the user wishes to view the three-dimensional image, and the image data is stored in the external file storage memory 88 in the form of a sheared volumetric image array, then the display module 92 retrieves the sheared volumetric image array from the external file storage memory. If the image data has not been stored in the external file storage memory 88, the display module 92 retrieves the image data stored in the memory 82 and retrieves the calibration file from the external file storage memory 88. In this case, once the display module 92 receives the image data and other related image data, it uses the data in conjunction with the shear transformation to display a three-dimensional image of the target volume on the screen 36a (block 128) with virtually no delay. The displayed image can be manipulated by the user as will be descried. During image manipulation, the user can store displayed views in the memory 82 or in the external file storage memory 88 so that these views can be retrieved and re-examined at a later time. Once image manipulation has been completed, the user is prompted to confirm whether another three-dimensional image is to be created (block 130). If the user wishes to create another three-dimensional image, the system 20 reverts to block 102. Otherwise, the three-dimensional imaging procedure is considered to be completed.

If at block 126, the user does not elect to view the three-dimensional image, the system proceeds directly to block 130.

Three-Dimensional Image Display

Figure 6:
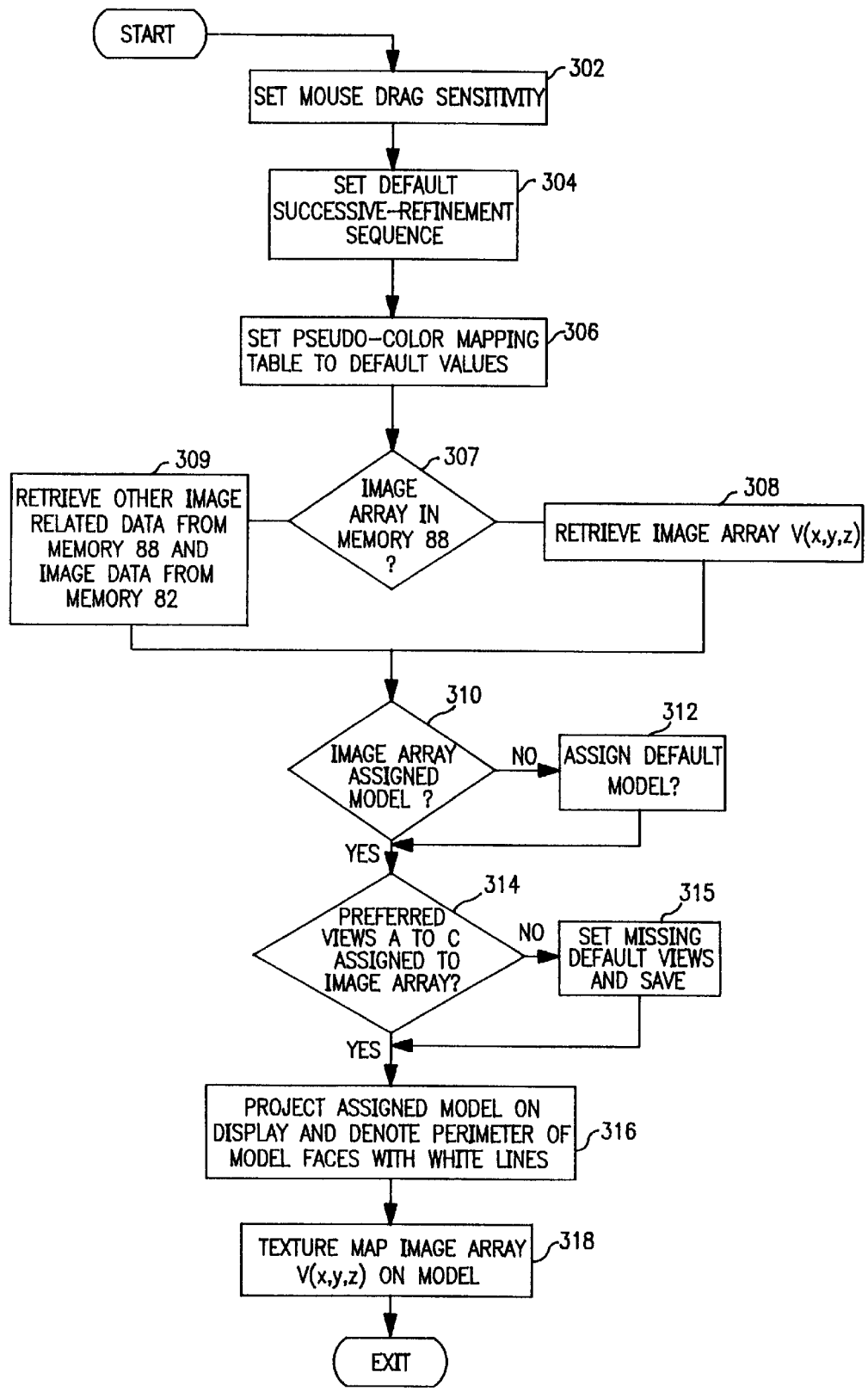
FIG. 6 shows a flowchart of steps performed by the display module during initialization.

Once the two-dimensional images of the target volume have been acquired and have been stored either in external file storage memory 88 with the calibration file as a sheared volumetric image array or in physical memory 82, the user can decide whether the three-dimensional image is to be displayed on the screen of monitor 36 using the graphical input device 38 (block 126). When the three-dimensional image is to be displayed as signified by the user via the graphical input device 38, the display module 92 enters an initialization routine (see FIG. 6). Upon entering the initialization routine, the display module 92 sets a number of parameters to their default values as will be explained and uses this information when an image is to be displayed on the screen 36a (blocks 302 to 306). The parameters which are set to their default value are mouse-drag sensitivity, successive refinement sequence and pseudo-color mapping.

After the above has been done, the display module 92 determines whether the image data has been stored with the calibration file as a sheared volumetric image array or resides in the physical memory 82. If the image data has been stored as a sheared volumetric image array, the display module 92 retrieves a copy of the sheared volumetric image array from external file storage memory 88 (block 308). If the image data resides in the physical memory 82, the display module retrieves the image data from the memory 82 and retrieves the other related image data in the calibration file from the memory 88.

Once the display module 92 has retrieved the image data and the other related image data, the display module 92 checks to see if the image data has been assigned a model (block 310). The model is in the form of a convex polyhedron having a plurality of planar faces defined in the same space as the three-dimensional image to be displayed. The polyhedron may take a variety of shapes as will be described herein.

If the image data has not been assigned a model, the dimensions of the image data are examined and a model in the form of a parallelepiped, which encloses substantially all of the pixels in the image data array is created and assigned to the image data automatically (block 312). The parallelepiped has two interior angles at right angles and a third interior angle equal to the angle $\alpha$. The assigned model is then saved in memory with the image data array. After this, the image data array is examined to determine if any or all preferred Views A to C have been assigned to the image data array (block 314). If some or all of the preferred Views have not been assigned, the preferred Views are created automatically and saved in the memory 82 with the image array (block 315).

Figure 13:
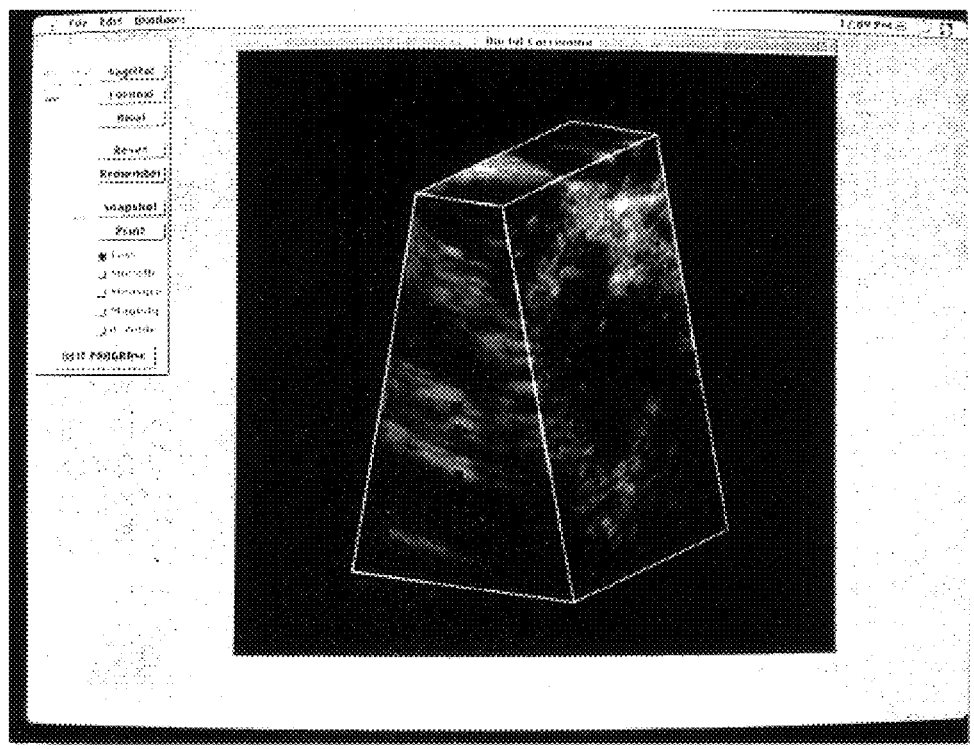
FIG. 13 shows a typical full screen display including a main display window and a control display window.

The model is then projected on the screen of the monitor 36 within a rectangular sub-region of the full screen display, henceforth called the "main display window" via an orthographic projection (block 316). FIG. 13 illustrates the screen 36a of monitor 36 on which the model and three-dimensional image are displayed within the main display window MDW. It should have been realized that other projection transformations such as a perspective projection may be used to project the model onto the screen. Only the visible faces of the model are displayed on the screen 36a, i.e., hidden-surface elimination is performed so that the displayed model has an opaque appearance. The perimeter lines of the model faces are depicted on the screen by white lines. Each visible model face is projected onto the screen within a polygonal area. Each visible face's polygonal area is divided into an internal area and an external area, the latter being the part of the total area immediately adjacent to the display boundary of the face and represents a small portion of the total area.

The display of each visible model face is accomplished as follows. Each screen pixel within the polygonal area of the displayed face has an associated two-dimensional cartesian coordinate pair $(x',y')$. With precise specifications of the model surface, this can be extended to a three-dimensional coordinate triple $(x',y',z')$.

By means of the shear transformation, the pixel co-ordinates $(x',y',z')$ may be converted to corresponding voxel coordinates $(x,y,z)$, to select a voxel value within the volumetric image array $V(x,y,z)$. The extracted voxel value is indexed into the pseudo-color mapping table to yield a gray-level or color. The gray-level or color in turn is used to illuminate the screen pixel. This process is repeated for all screen pixels located within the displayed model faces (block 318). This technique of display is called "texture mapping", and is known to those of skill in the art.

Each pixel on the display screen is identified by its associated cartesian coordinates $(x',y')$, which are usually integers. Each voxel in the volumetric image array is identified by its associated array indices $(x,y,z)$, which are also usually integers. For pixels within the perimeter of a displayed model face, it is possible to compute from the pixel coordinates $(x',y')$, a value $z'$ representing the distance from the plane of the screen 36a to the point on the model face which is projected onto that pixel. In the case of planar faces and using an orthographic or perspective projection, each displayed face has an associated plane equation $AX'+By'+Cz'=D$ which, given pixel coordinates $(x',y')$, may be solved to yield the corresponding depth value $z'$. Other techniques would be required for non-planar model faces, but in general, the problem remains one of solving an equation.

The correspondence between display coordinates $(x',y',z')$ and volumetric image coordinates $(x,y,z)$ is given by the shear transformation. The particulars of the shear transformation are re-computed whenever the user decides to change one or more view parameters such as angle of view, display scale, etc. In the case of an orthographic projection and image data arrays sampled on a regular cartesian grid, the viewing transformation is a simple linear mapping. For other cases, such as a perspective projection and/or non-cartesian sampling geometries, the viewing transformation may be more complex. The image coordinates $(x,y,z)$ computed from display coordinates $(x',y',z')$ via the shear transformation will not generally be integers, and hence, will not correspond to individual image voxels. In such cases, a voxel value must be computed by interpolation from the nearest available image voxels. This process is called re-sampling, and is known to those of skill in the art. Those of skill in the art will furthermore be aware that a variety of interpolation techniques or "re-sampling methods", are known, and will be aware of their relative advantages and drawbacks.

The preferred embodiment of the present invention performs the display process in multiple passes, using computationally inexpensive re-sampling methods in earlier passes and progressing to slower, more accurate methods in later passes. It also permits the user to enable or disable selectively, individual passes to choose a satisfactory trade-off between rapidity of response and image fidelity.

Furthermore, it is preferred that later passes be interruptible so that if the user requests rapid change of the displayed view, only the earliest passes are performed until such time as there is a pause in user input. At this point, the later passes are performed on the final view only. This technique is called successive refinement and is known to those of skill in the art.

After the three-dimensional image and the model are displayed on the screen 36a of the monitor 36, the initial view is saved in the memory 82 with the image data array and is indexed as the "Reset" view. Therefore, after initialization, four saved views of the image data array exist and can be retrieved from memory and displayed when an associated icon is selected as will be described. It should be apparent that the number of saved views is arbitrary and that fewer or more saved views may be created and saved. When the initialization is complete, the display module 92 begins to monitor continuously the graphical input device 38 to detect input commands representing desired manipulations to be performed on the displayed image (see FIGS. 7a to 7d). When input commands are detected by the display module 92, the display module manipulates the displayed image in accordance with the received input commands.

Although the display module 92 has been described as retrieving the two-dimensional ultrasound image data from the physical memory 82 and the other related image data from the memory 88 after the entire target volume has been scanned, it should be appreciated by those of skill in the art that the calibration file may be retrieved by the display module 92 prior to acquisition of the two-dimensional ultrasound image data. In this case, the other related image data in the calibration file does not describe acquired two-dimensional ultrasound image data per se but rather describes the memory location and characteristics of the structure in physical memory 82 into which the two-dimensional ultrasound images will be captured. When the system is operated in this manner, the display module 92 is able to present a three-dimensional image of the target volume virtually simultaneously as the target volume is being scanned.

Although the system 20 has been described as moving the ultrasound probe 24 along a linear scanning path Z, it should be realized by those of skill in the art that other ultrasound probe scanning geometries may be used. In these instances, the other related image data in the calibration file must be altered to take the scanning geometry into account so that a relatively simple transformation may be used to convert the two-dimensional image data into a volumetric image array.

Three-Dimensional Image Manipulation

All manipulations of the displayed image can be executed via three actions using the graphical input device 38. These actions are termed "point", "click" and "drag". To "point" is to move the graphical input device 38 so that the cursor is positioned on the screen 36a at a desired region without depressing its button. To "click" is to press down on the button of the graphical input device while to "drag" is to move the graphical input device while the button is depressed. The term "point-click-drag sequence" is used to denote the complete action of moving the cursor into a desired region on the screen via the graphical input device, depressing the button on the graphical input device, moving the graphical input device to another desired region with the button depressed and then releasing the button. Specific manipulations of the image are carried out according to the region in which the click aspect of the point-click-drag sequences occur.

Once the initialization routine has been completed and the model and three-dimensional image are displayed on the screen, the graphical input device is monitored to determine whether the user wishes to manipulate the displayed image. The manipulations supported by the display module 92 are rotation of the entire model and three-dimensional image about an arbitrary axis, translation of a selected plane of the model and rotation of a selected plane of the model about an arbitrary axis. The manner in which the display module 92 interprets movement of the graphical input device 38 and manipulates the displayed model and image in response to the graphical input device 38 will now be described.

The display module 92 continuously monitors the graphical input device 38 to determine the position of the cursor on the screen and to determine if a click has occurred. Specifically, the display module 92 determines if the cursor is located within the exterior area of a visible model face (block 324). If the cursor is positioned within such an exterior area, the display module 92 colors the perimeter lines of that model face blue (block 326). Otherwise, the display module 92 changes the color of any perimeter lines which may have been blue to their previous color (block 328). The display module 92 also determines if a click has occurred (block 330). If a click has not occurred, the movement of the graphical input device 38 is tracked. The display module 92 moves the cursor on the screen 36a to follow the movement of the graphical input device (blocks 332 and 334). As the cursor is moved, the display module 92 reverts back to block 324 so that the perimeter lines of the visible faces change colors depending on the location of the cursor as just described.

When a mouse click is detected, the position of the cursor on the screen 36a is examined to determine if the cursor is located within the main display window (block 336). If the cursor is outside of the main display window, the display module 92 determines if the cursor is positioned over an option icon (block 338). If the cursor is not over an option icon, the click is ignored and the graphical input device 38 is monitored until the button is released (block 339). At this time, the display module 92 reverts back to block 324. If however, the cursor is positioned over an option icon, then the display module 92 executes a routine associated with the selected option icon as will be described.

When a graphical input device click occurs and the cursor is positioned within the main display window as detected at block 336, the display module 92 determines whether the cursor is located within the interior area or exterior area of a displayed model face or in the background (block 340). If the cursor is located in the background, the display module 92 determines that the user wishes to rotate the entire model and three-dimensional image. In this case, after the button has been depressed, the drag direction and drag distance of the graphical input device 38 is monitored (block 342). As the graphical input device 38 is being dragged, the drag direction and drag distance are repeatedly conveyed to the display module 92 (block 344). The drag distance and drag direction values are used by the display module 92 to rotate the three-dimensional model and image and to update the display to show the rotation on the screen (block 345). Once the button on the graphical input device 38 has been released, the manipulation is considered complete and the display module 92 reverts to block 324 (block 346).

A variety of techniques for converting mouse drag distance and direction to three-dimensional rotation axis and angle parameters are known to those skilled in the art. The preferred embodiment of the present invention uses Shoemake's "Arcbal" technique described in the Proceedings of Graphics Interface 92 published by the Association For Computing Machinery (ACM). The fixed point of rotation for the three-dimensional image is constrained to be the geometric center of the initial model. Thus, in this manipulation, movement of the graphical input device vertically on the screen 36a through the center of the displayed image causes the displayed image to rotate about a horizontal axis, while movement of the graphical input device horizontally through the center 34 of the image causes the displayed image to rotate about a vertical axis.

Figure 8A:
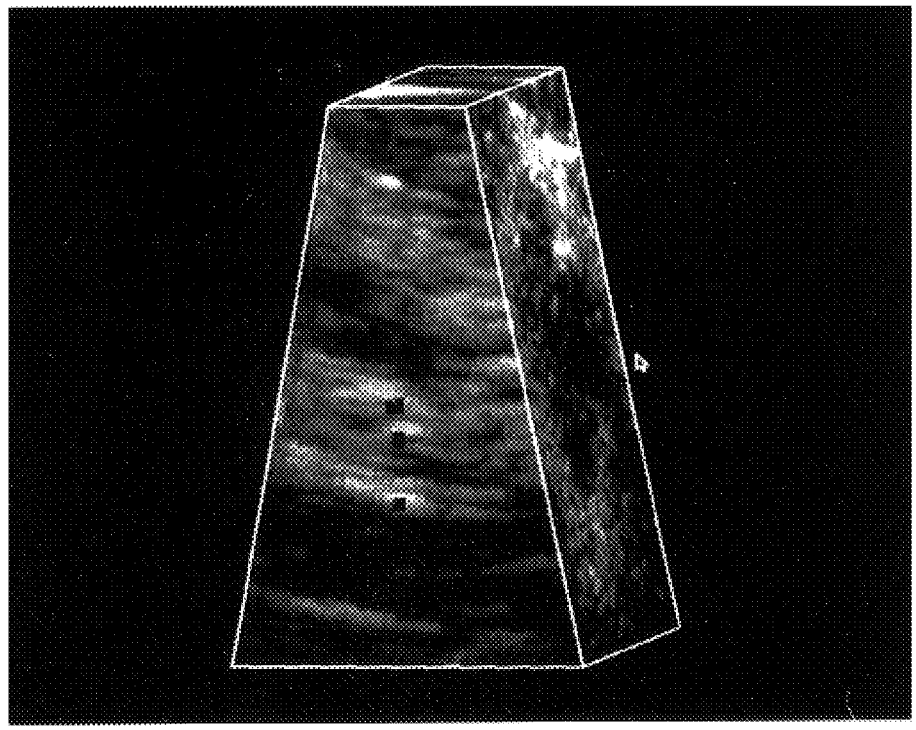
FIGS. 8a to 8c show a three-dimensional image and model undergoing a rotation about a vertical axis.
Figure 8B:
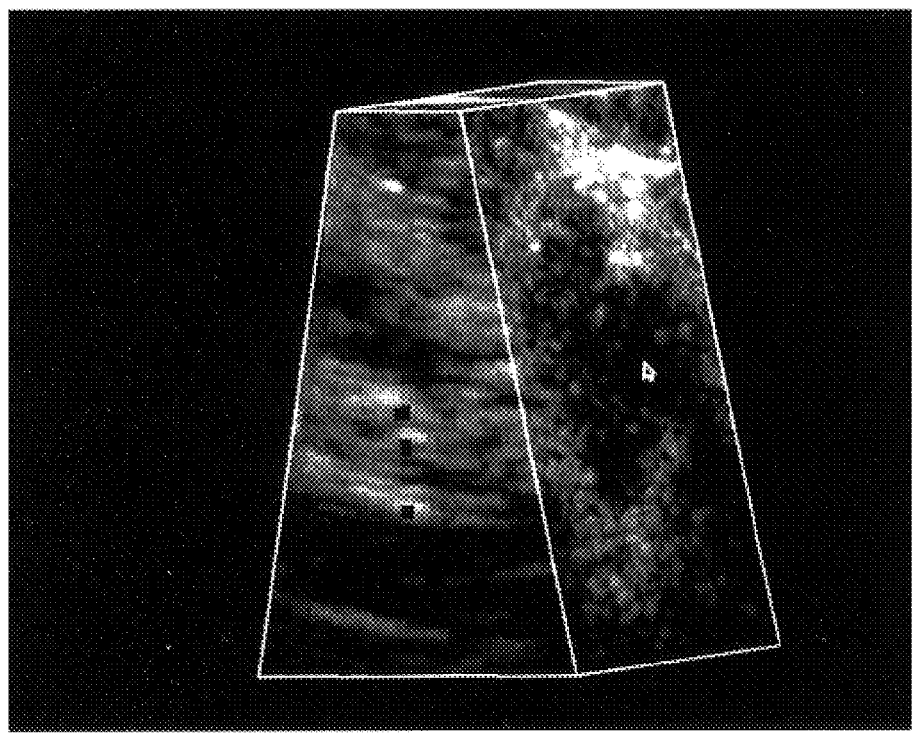
Figure 8C:
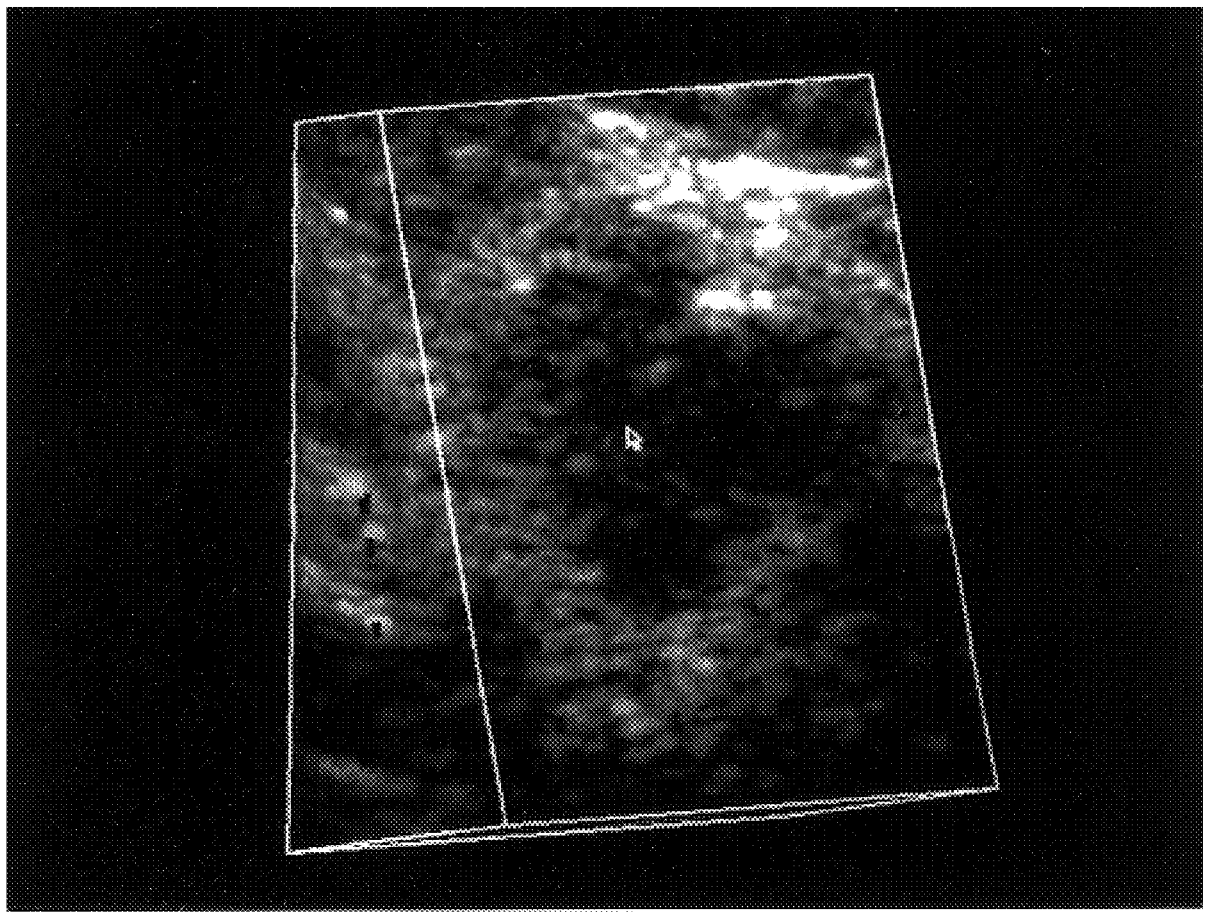
Figure 9A:
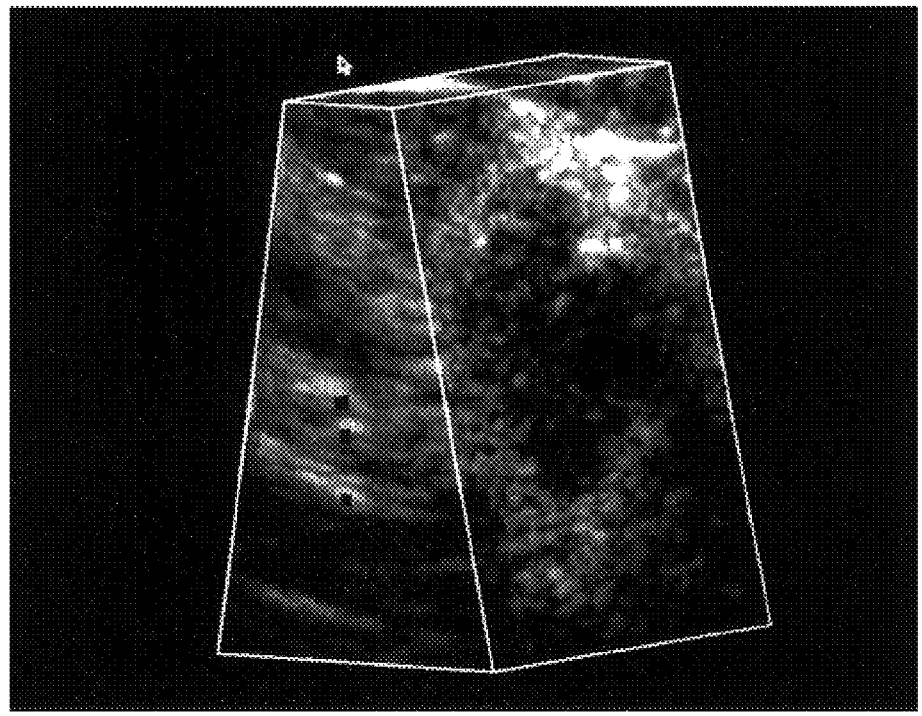
FIGS. 9a to 9c show a three-dimensional image and model undergoing a rotation in a direction from top-left towards bottom right about an axis, angled at about 30° to the horizontal and sloping up and to the right.
Figure 9B:
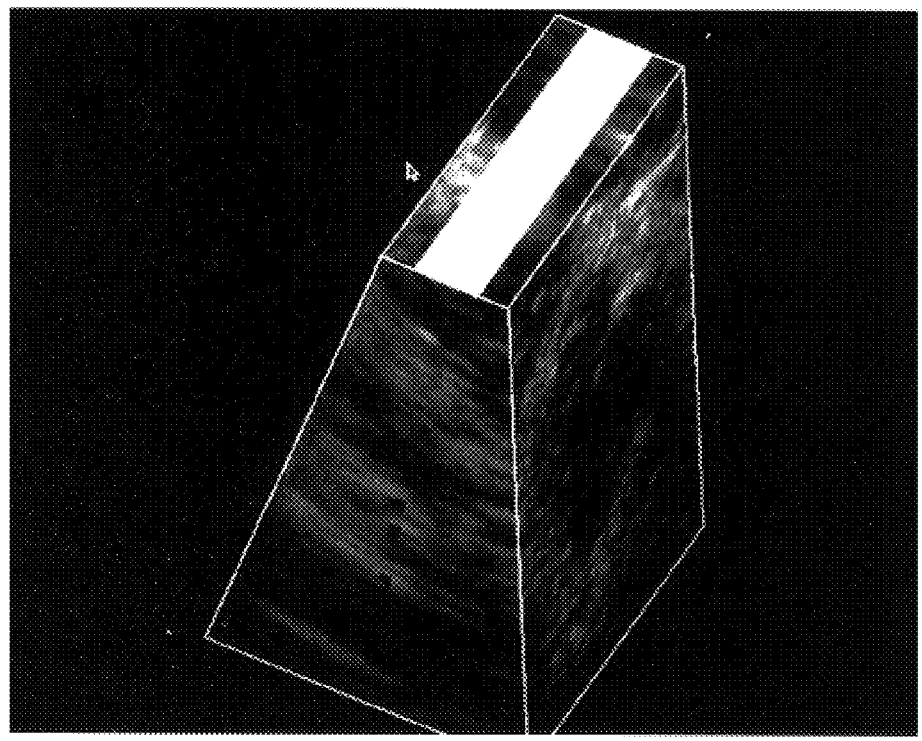
Figure 9C:
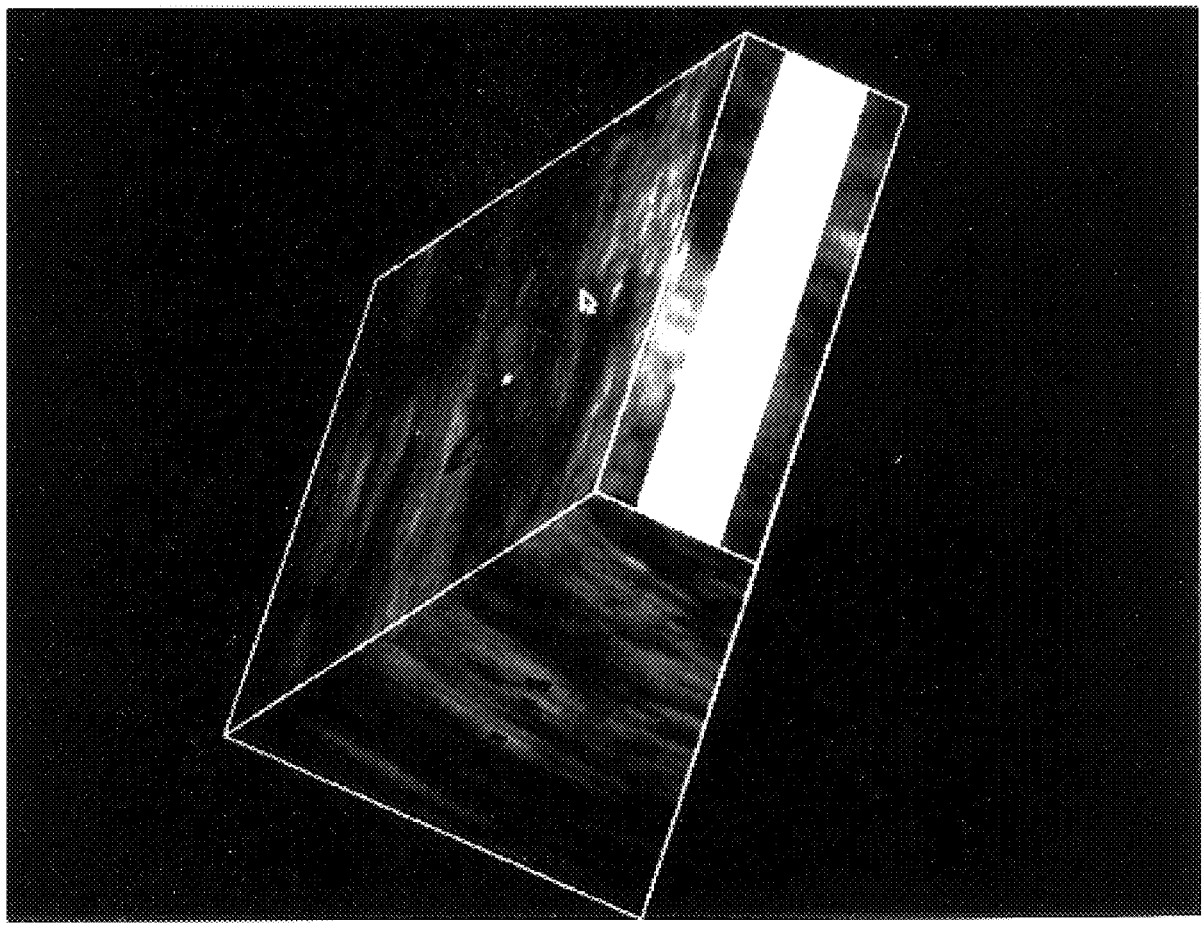

FIGS. 8a to 8c show the model and three-dimensional image within the main window display undergoing a rotation about a vertical axis as the graphical input device 38 is moved to drag the cursor across the main display window from mid-right to mid-lift. FIGS. 9a to 9c show the model and three-dimensional image undergoing a rotation about an axis, angled at about 30° to the horizontal and sloping up and to the right, as the graphical input device 38 is moved to drag the cursor across the main display window from top-left to bottom-right. As should be apparent, this operation gives the user the sense of taking hold of the displayed image and pulling it around. Further details of this image manipulation can be found in the above-mentioned publication.

To facilitate understanding of manipulations of the model other than simple rotation of the entire model, it is necessary to describe the polyhedral model in greater detail. Mathematically, a convex polyhedron can be characterized as the intersection of a set of half-spaces defined by at least four planes, herein called bounding planes. Each face of the polyhedron is a convex polygon embedded in the corresponding bounding plane. By changing the parameters of the bounding planes (i.e. The coefficients the display module 92 either to retrieve a copy the sheared volumetric image array from the memory 88 A,B,C,D in the plane equation $Ax+By+CA=D$), the shape of the model polyhedron can be modified. The number of bounding planes may also be changed. Specifically, new bounding planes may be added and existing planes removed from the mathematically specification of the model. The result is that the model polyhedron gains or loses faces.

The display module 92 supports two primary manipulations of bounding plane coefficients, namely translation (change of coefficient D, which essentially specifies the perpendicular distance from the plane to the coordinate origin) and rotation (change of coefficients A,B,C, which collectively specify the orientation of the plane relative to the coordinate axes). As will be described below, the choice of which bounding plane (and hence which corresponding model face) is to be affected, and whether to perform translation or rotation, is determined by contextual interpretation of point-click-drag sequences relative to the displayed model. The display module 92 also provides means to add and delete bounding planes from the model specification, as will also be described below.

A distinction is made between original bounding planes, which are aspects of the model assigned to the volumetric image array V(x,y,z) when it is first loaded into memory (blocks 310 and 312 in FIG. 6) and planes added in response to user input. Model faces corresponding to original bounding planes have their perimeter lines displayed as white lines, while faces corresponding to added planes are indicated using another color, typically yellow or green. Only added planes may be translated, rotated or deleted. The original planes represent the boundaries of the volumetric image and, provide the means to support the addition of new planes.

Figure 7A:
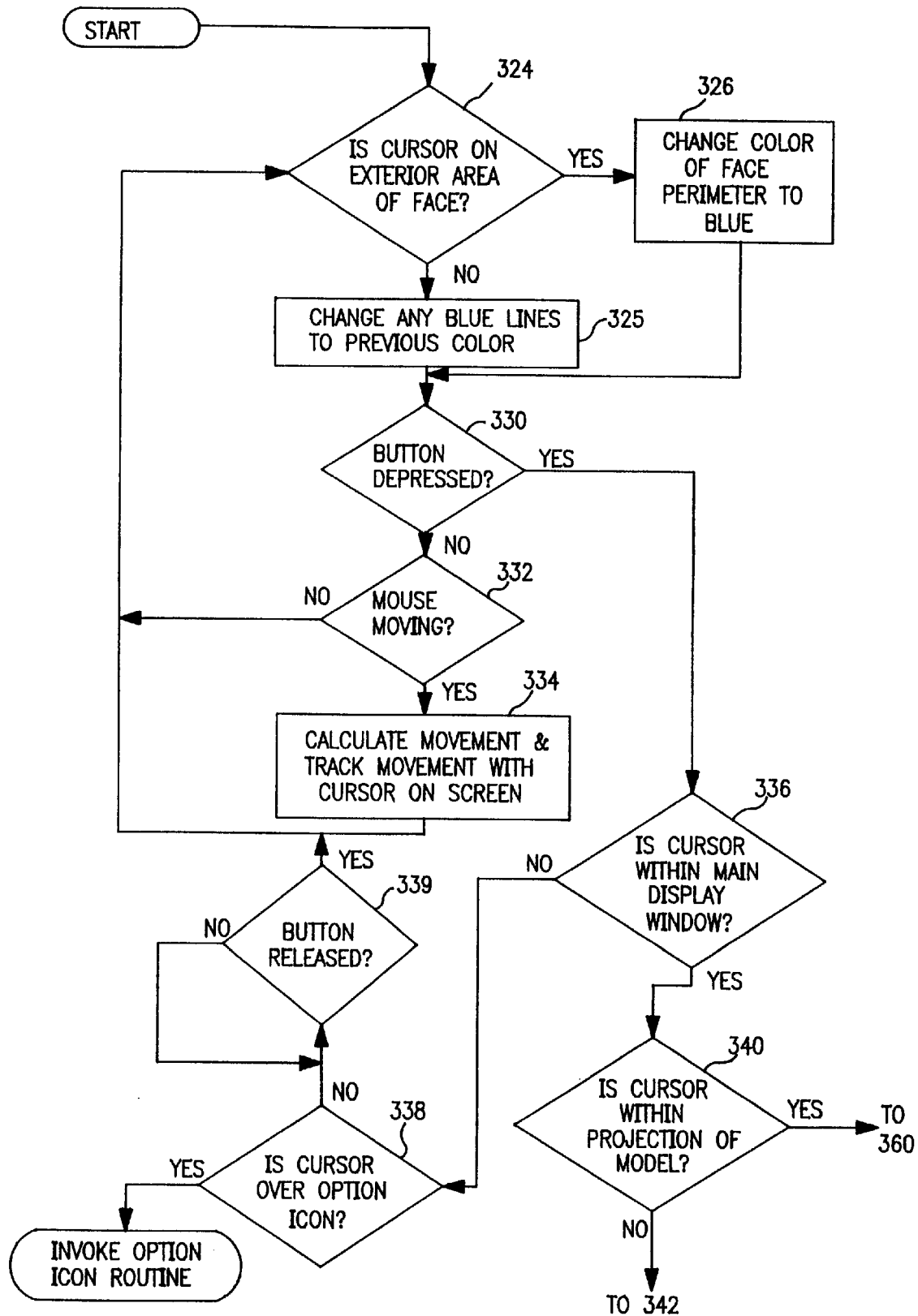
FIGS. 7a to 7d show flowcharts of steps performed by the user interface and display modules when manipulating a displayed three-dimensional image.
Figure 7B:
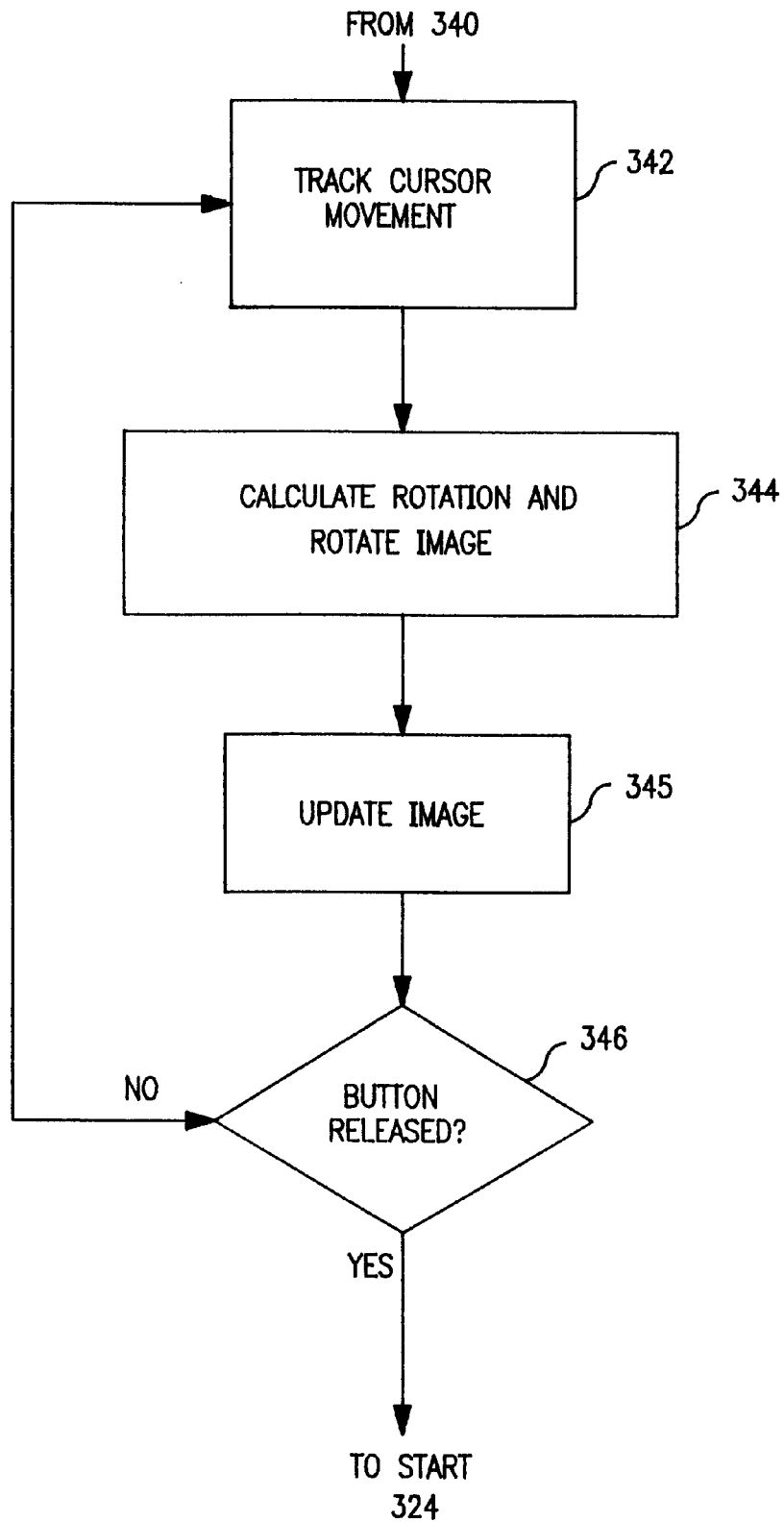
Figure 7C:
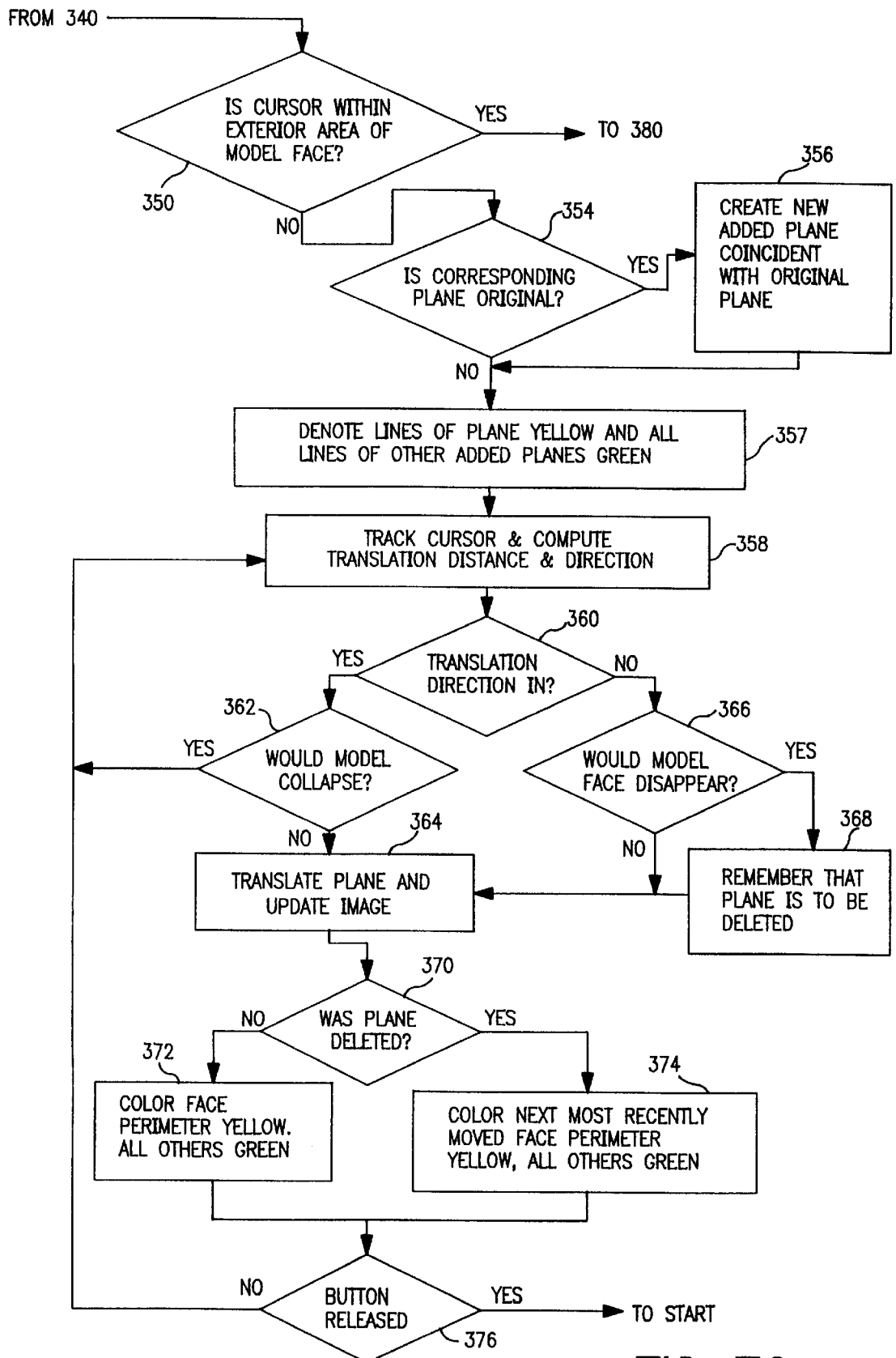
Figure 7D:
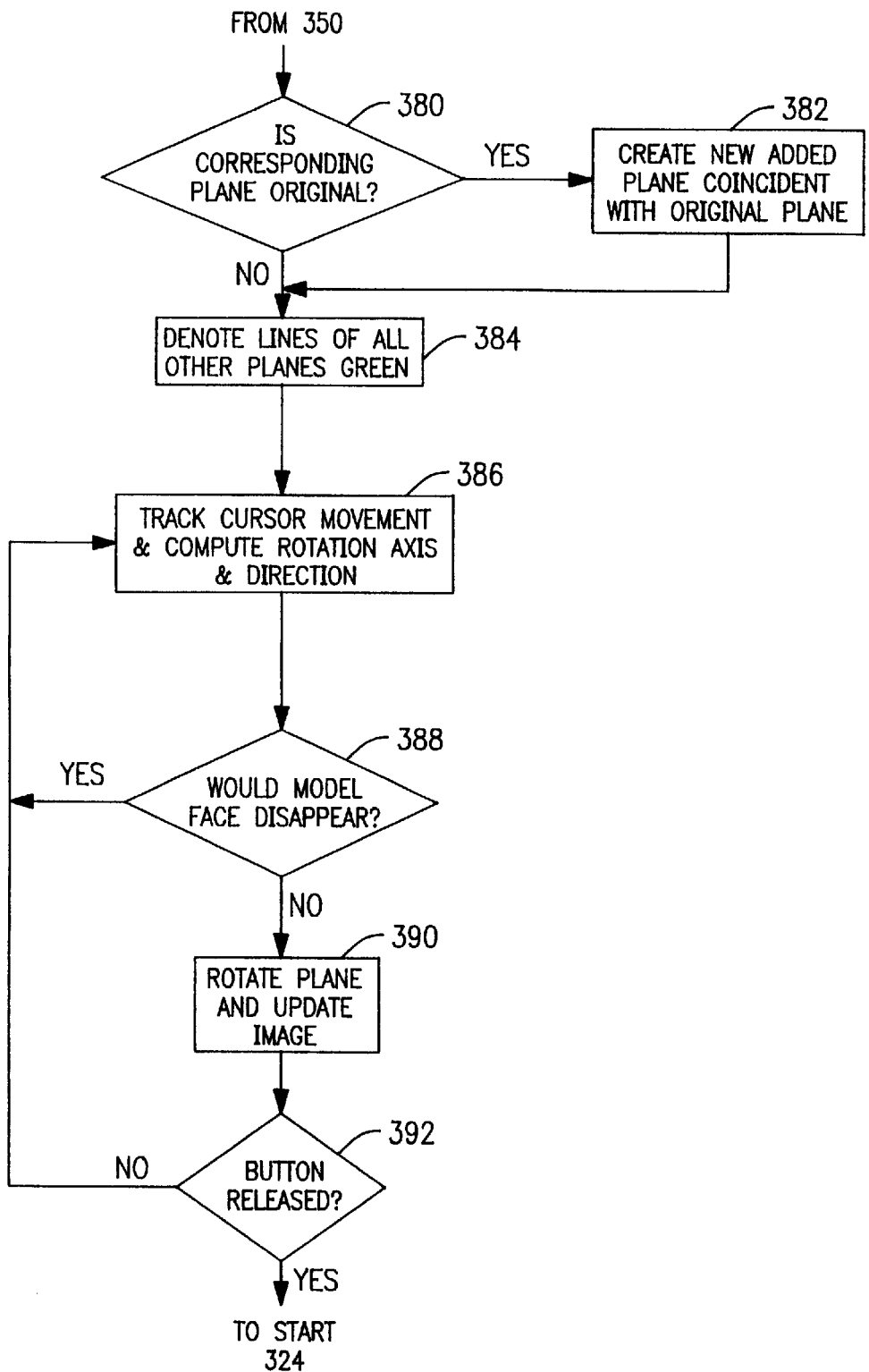

If at block 340, the click is detected and the cursor is determined to be within the perimeter of a displayed model face, the face of the model in which the cursor is positioned is determined and the position of the cursor within the face is examined by the display module 92 (block 350 in FIG. 7c). If the cursor is positioned within the interior area of the face, the display module 92 determines that it is desired to translate the corresponding bounding plane. Thereafter, the display module 92 examines the corresponding plane to determine whether the plane is an original plane i.e. one denoted by white lines (block 354). If the plane is an original plane, a new plane is created and added to the model (block 356). Initially, the added plane is congruent to the original bounding plane. Once the added plane has been created or if at block 354, the plane is not an original plane, the perimeter lines denoting the plane (i.e. The perimeter of the corresponding displayed model face) are colored yellow and all perimeter lines of other added planes are colored green (block 357).

The drag distance and direction of the graphical input device are then monitored (block 358). The display module 92 next determines the direction of translation of the added plane. To do this, the display module 92 calculates the dot product of the drag vector and the projection onto the screen 36a of a normal vector to the plane is computed. If the dot product is positive, the plane is translated in the direction of the normal vector; if negative, it is translated in the opposite direction. In the preferred embodiment, the model specifications are such that all boundary plane normal vectors point away from the interior of the model polyhedron. Hence, movement of the graphical input device 38 which results in a positive dot product pulls the plane outward from the center of the model, while movement of the graphical input device 38 which results in a negative dot product pushes it in (block 360).

If the translation direction of the plane is determined to be in, the display module 92 checks to ensure the translation does not result in the collapse of the model (block 362). If it does, the display model 92 reverts back to block 358 without updating the displayed model and three-dimensional image. Otherwise, translation of the added plane occurs, and the points in the volumetric image array V(x,y,z) which correspond to those on the translated plane are texture-mapped onto the plane (block 364).

If a block 360, the translation direction is determined to be out, the display module 92 checks to see if the translation can result in the plane disappearing (block 366). If not, the display module 92 proceeds to block 364 and updates the displayed model and three-dimensional image. Otherwise, the display module 92 notes that the translation may result in the disappearance of the plane before proceeding to block 364 (block 368). As should be apparent, as a plane is translated, various cross-sections of the image can be viewed as the translated plane slices through the volumetric image array V(x,y,z). Once the plane has been translated, the display module checks to see i the plane was deleted (block 370). If not, the perimeter lines of the translated plane are colored yellow and all other perimeter lines are colored green (block 372). Otherwise, the perimeter lines of the next most recently modified plane are colored yellow and all other perimeter lines are colored green (block 374). When the button is released, the display module 92 considers the translation manipulation complete and reverts back to block 324 (block 376).

Figure 10A:
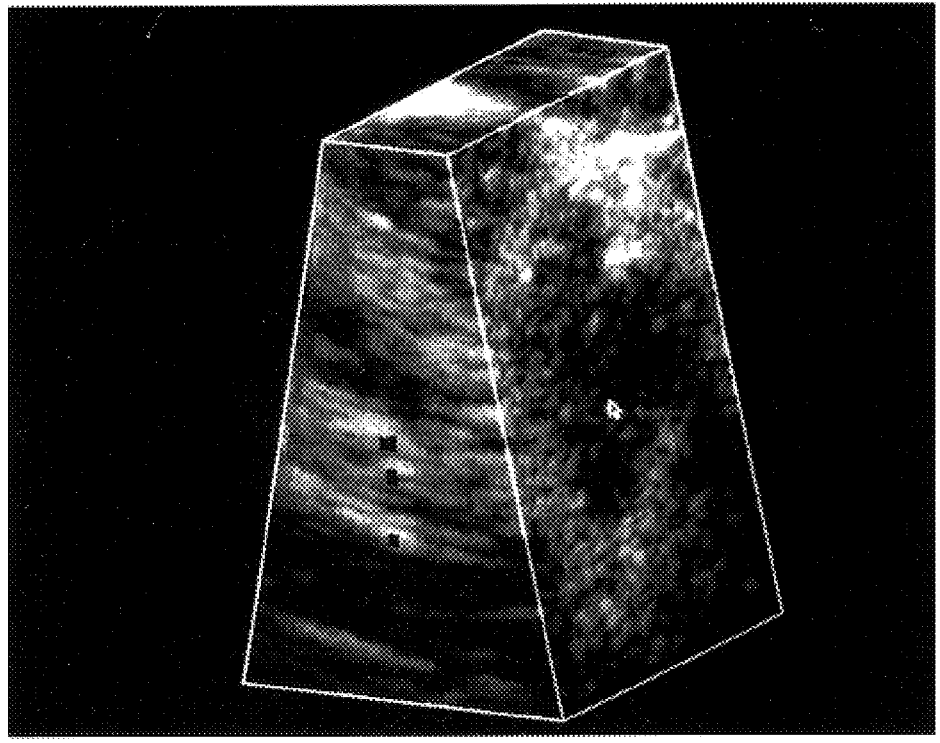
Figure 10B:
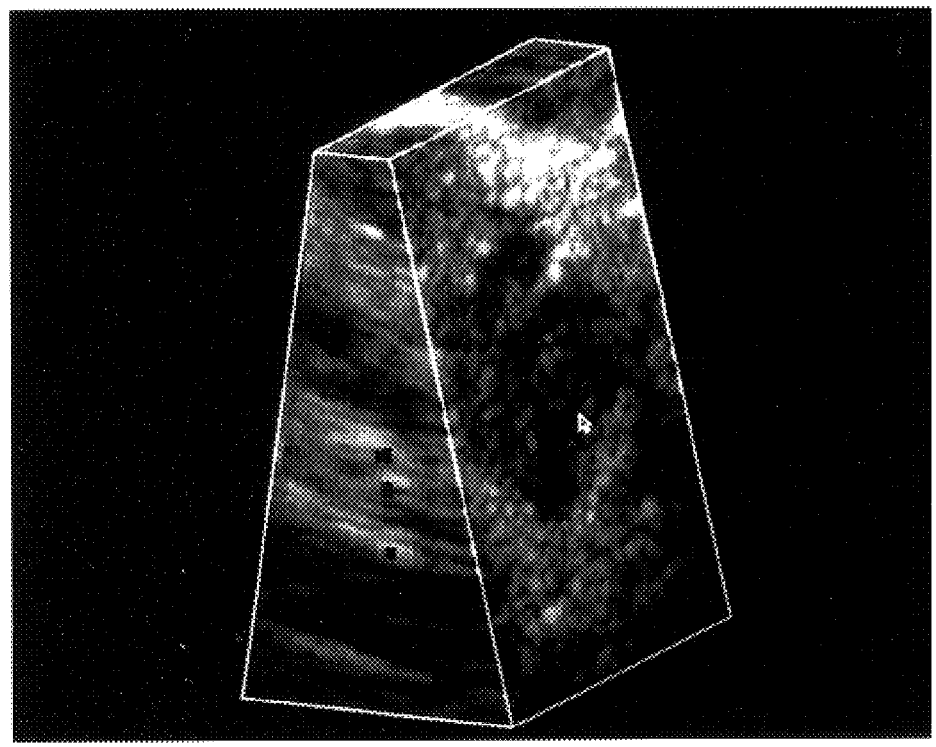

When the added plane which is to be translated is nearly parallel to the plane of the screen 36a, the dot product described above is essentially zero. In such cases, the display module 92 only considers the vertical component of the graphical input device movement to determine the translation direction and distance. In this instance, upward movement of the graphical input device 38 causes the display module 92 to push the added plane into the model 36a while downward movement of the graphical input device causes the display module to pull the plane out of the model. FIGS. 10a to 10c show the model and image within the main display window, wherein a plane of the model is translated towards the geometric center of the model.

When a click is detected and the cursor is positioned within the exterior area of a model face as determined at block 350, the display module 92 determines that the corresponding bounding plane is to be rotated. The display module then examines the plane to determine whether the plane is an original plane (block 380). If the plane is an original plane, a new plane congruent to the original plane is created and added to the model (block 382). The perimeter lines of the added plane are colored yellow. Once this has been done or if at block 380, the plane is not an original plane, the perimeter lines of all other added planes are colored green (block 384).

Figure 11A:
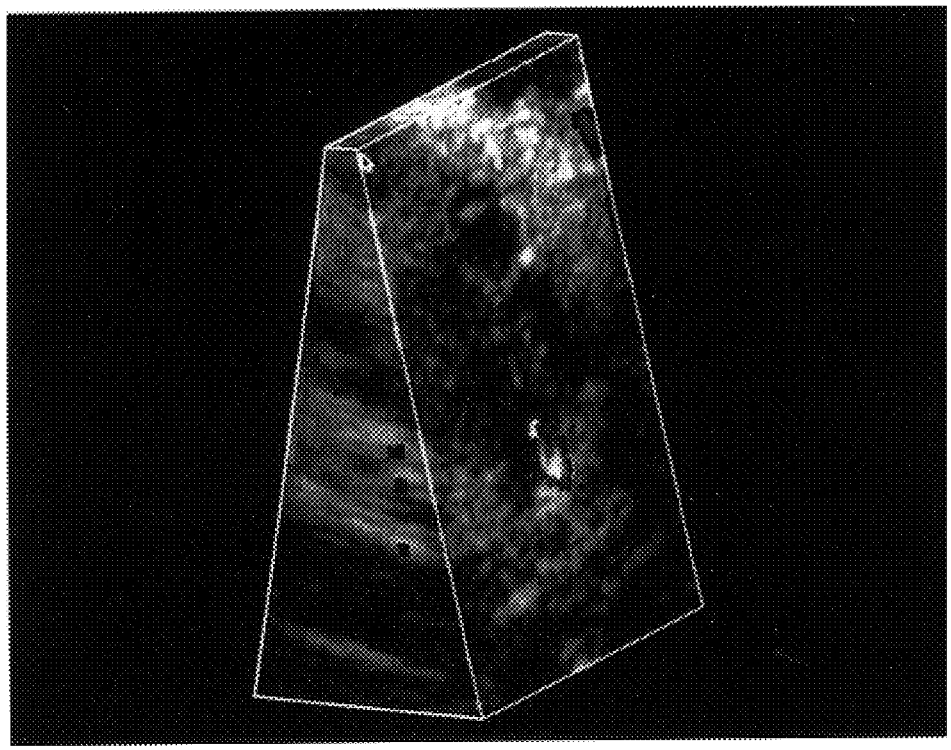
Figure 11B:
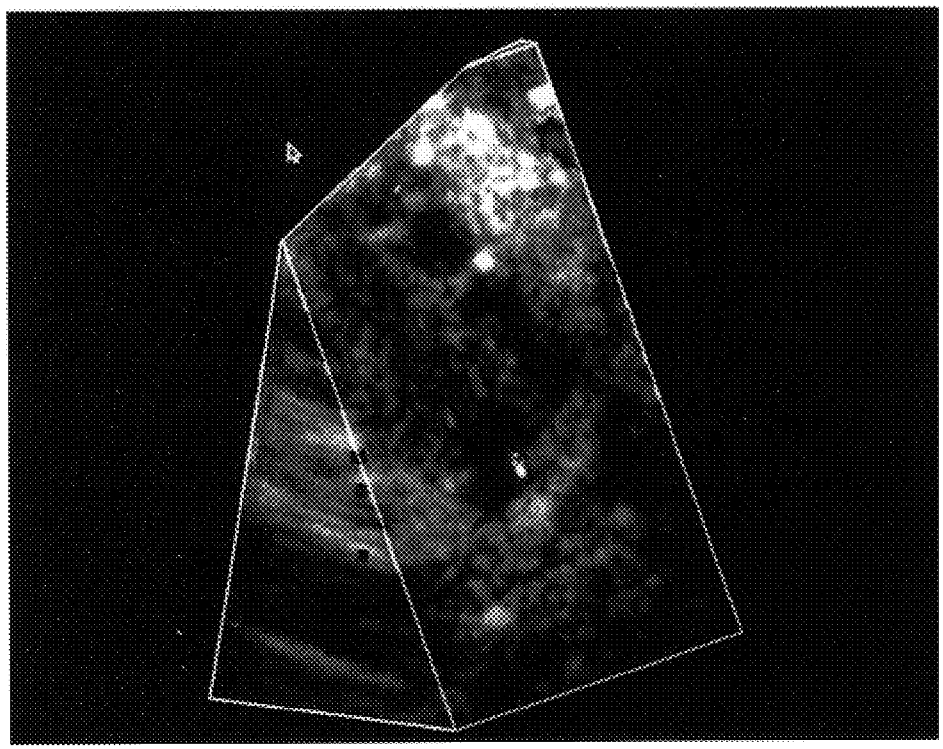
Figure 12A:
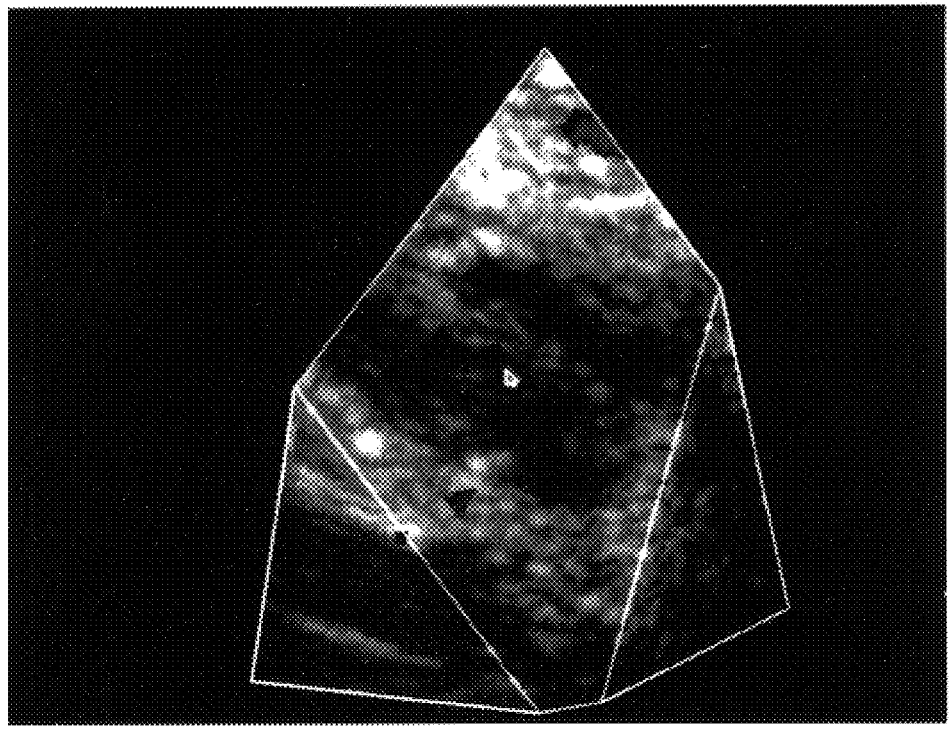
FIGS. 12a to 12d show a three-dimensional image and model in which a plane of the model is translated away from eh geometric center of the model until it disappears.
Figure 12B:
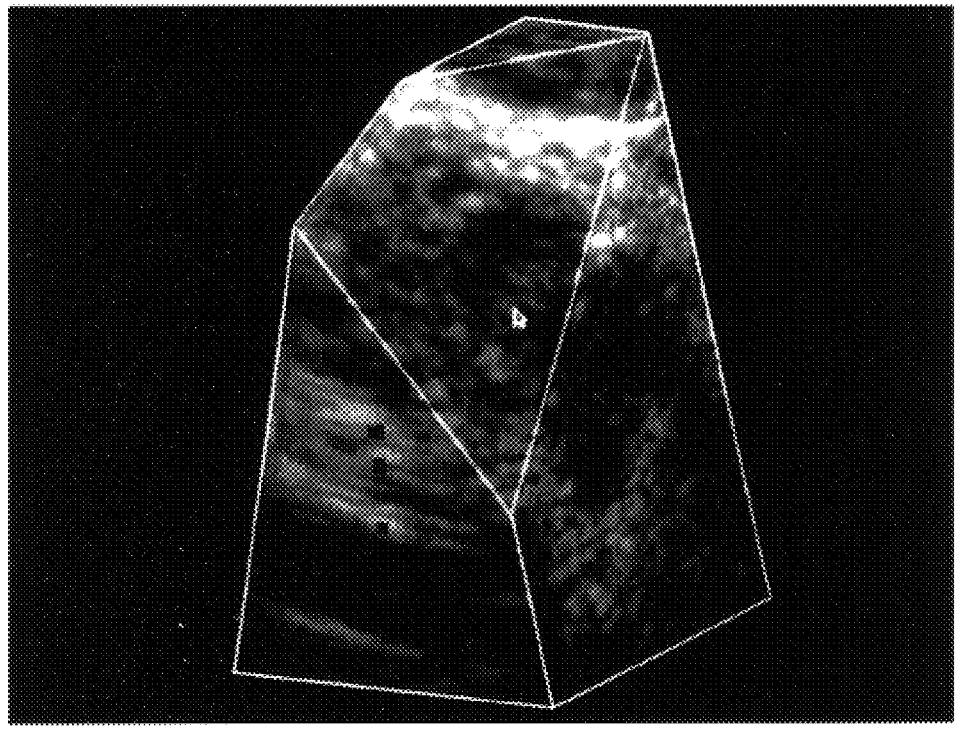
Figure 12C:
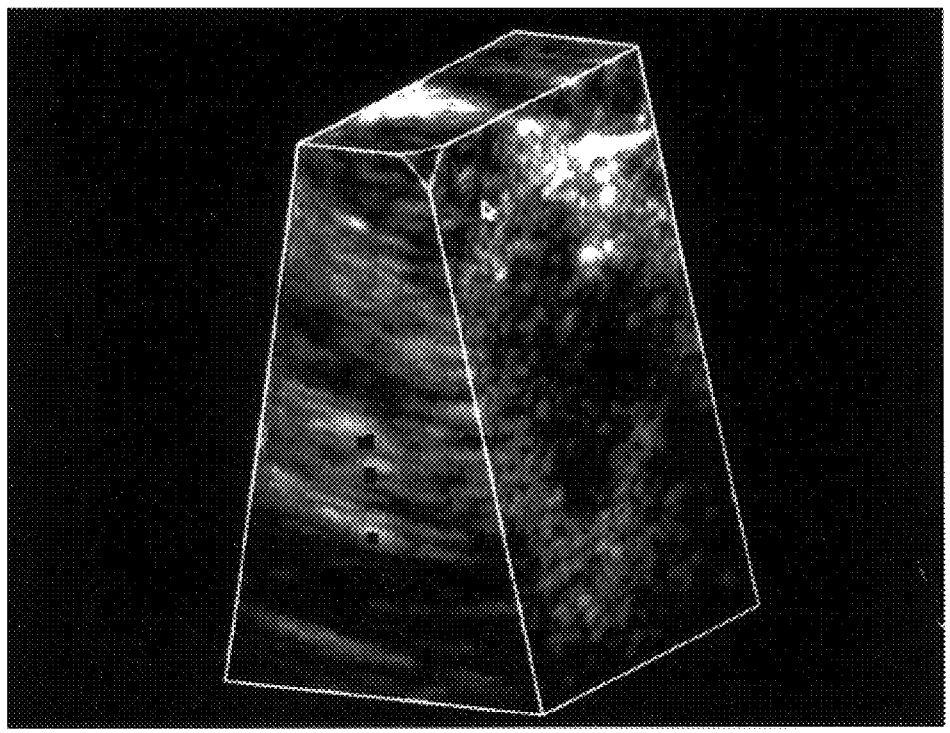
Figure 12D:
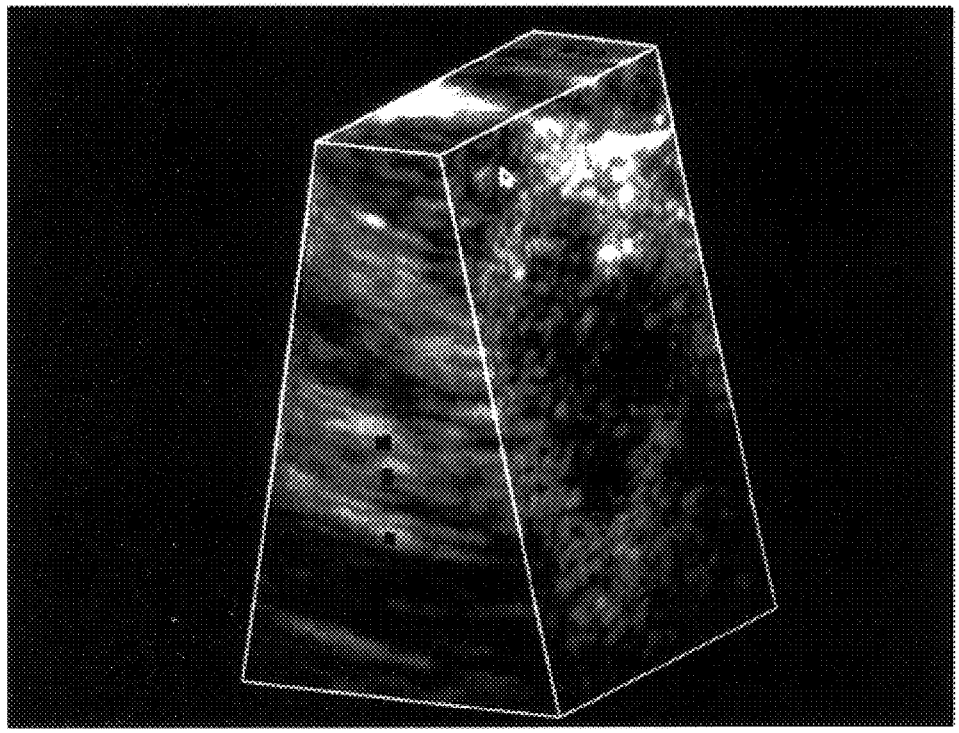

After this, the drag distance and direction of the graphical input device 38 are monitored and the rotation axis and direction of the graphical input device are computed by the display module 92 using Shoemake's technique referred to previously (block 386). After this, the display module 92 determines whether the rotation would cause the plane to disappear (block 388). If so, the display module 92 reverts back to block 386 without updating the display model and three-dimensional image. Otherwise, the display module 92 rotates the added plane about the geometric center of the initial model by the calculated amount. As the rotation is occurring, the display module 92 updates the image on the screen (block 390). This allows different cross-sections of the image to be viewed as the rotated plane slices through the volumetric image array V(x,y,z). FIGS. 11a to 11c show the model and three-dimensional image within the main display window, wherein a plane of the model is rotated about an axis, angled at about 30+ to the horizontal and sloping up and to the right. It is through this manipulation that new oblique planes may be added to the model. Once the button on the graphical input device 38 has been released signifying that the plane rotation has been completed, the display module 92 reverts to block 324 (block 392).

As should be apparent from the above description, whenever original planeses of the model are selected by the user to be translated or rotated, added planes are created and it is the added planes which are moved. The original planes, although not shown on the display screen, remain stored in memory 82 and may be recalled at any time to reset the display to its original state. It should also be apparent that white lines denote an original plane, green lines denote and added plane with the exception of the last moved plane which is denoted by yellow lines and blue lines denote that the plane is going to rotate if a mouse-drag sequence occurs.

When an added plane is rotated, the added plane may become oblique but it is not permitted to extend beyond the boundary defined by the original planes (see FIGS. 11a to 11c). Any added plane can be translated sufficiently far out of the model that its corresponding model face disappears. If the user releases the graphical input device button after the face has disappeared, the plane is removed from the model. This allows a user to delete unwanted added planes. If the graphical input device button is not released, the user can push the added plane back into the model so that the plane becomes visible again and no deletion takes place. FIGS. 12a to 12d show the model and three-dimensional image within the main window display wherein an oblique plane of the model is translated away from the geometric center of the model until it disappears. Although it would seem that if an added plane is translated sufficiently into the model, the entire model can collapse, the display module 92 does not permit an added plane to be translated so far as to collapse the model (see block 362).

While the graphical input device 38 is being moved to effect changes in the displayed view and the display is updated showing intermediate positions and orientations of the affected plane or planes, the display module 92 must re-sample the volumetric image array V(x,y,z) and complete the texture mapping process, a process of discrete approximation. In this embodiment, a number of re-sampling methods are available, each of which offer a different compromise between computational speed and image quality.

To achieve smooth operation with limited computer power, the display may be computed (rendered) at less than the full resolution of the monitor screen and/or a simpler interpolation technique may be employed in the re-sampling process. In this embodiment, the display is computed in as many as three rendering passes, the first and third of which may be disabled if the user so wishes, by selecting the appropriate option icon via the graphical input device 38. The enabled/disabled status of each pass is what is actually set to a default state at block 324 during initialization. The first enabled pass in the sequence is uninterruptible, i.e. while the graphical input device is being moved, the first enabled pass is performed in its entirety, yielding a succession of complete views on the screen. Subsequent enabled passes are automatically interrupted by graphical input device movement, the visible result being that the displayed view is only replaced by a higher quality view (computed by an interruptible rendering pass) when there is a sufficient pause in graphical input device movement. The three rendering passes supported by the present embodiment are:

1. reduced image reduction, nearest-neighbour re-sampling
2. full image resolution, nearest-neighbour re-sampling
3. full image resolution, tri-linear interpolation re-sampling As mentioned previously, at block 338, if a click is detected and the cursor is not positioned in the main display window, the display module 92 determines whether an option icon has been selected. The available option icons allow the user to select parameters different from the default values, to enhance image display and to execute special feature routines. These options icons include "Reset", "Views A to C", "Remember", "Snapshot", "Animation", "Indicator", "Orientation", "Fast", "Smooth", "Win", "Lev", "Magnify" and "Measure". FIG. 13 illustrates most of these option icons in a control display window positioned beside the main display window. In this example, the preferred Views A to C have been labelled by the user as "Sagital", "Coronal" and "Axial". The available options which can be selected via an option icon will now be described.

If the Reset icon is selected, the original view of the image and model stored with the volumetric image array V(x,y,z) is recomputed and displayed on the screen. Likewise, if one of View A to C icons is selected, the corresponding preferred view is recomputed and displayed. If the user wishes to change one or more of the Views A to C for a current session, the user can substitute the displayed view for the stored view. The present embodiment permits the user to activate a distinct window in which the View icon labels (e.g. Sagittal, Coronal, Axial etc. in FIG. 13) are displayed and to edit the labels as desired. Changes made to the labels persist only for the current session, unless the user elects to save the changes in memory 88 using an option icon provided for that purpose, in which case any preferred Views associated with the data file are overwritten.

If the Remember icon is selected, the current view on the screen is stored in memory 82 overwriting the "Reset" view for the current session only. The "Reset" view associated with the current data file in memory 88 is not changed, only the copy in memory 82. This view may be recalled to the screen at any time by selecting the Reset icon, unless and until it is overwritten by a subsequent use of the Remember icon.

It should be realized that a similar two-icon technique can be used for Preferred Views A to C. However, the present embodiment allows the user to overwrite these views in memory 82 by holding down a specified key on the keyboard while selecting the corresponding View icon.

If the Snapshot icon is selected at any time during manipulation of the model and image, the image currently displayed in the main display window is stored as a file in memory 88 in an industry-standard image file format, in order that it be may subsequently be used with other software. The present embodiment uses a tagged image file format ("TIFF"). If should be realized that adding support for other file formats can be achieved in a straightforward manner by following published format specifications.

If the Animation icon is selected, animated sequences of displayed views can be created and saved into memory 82 in an industry-standard image format as just described. When the Animation icon is selected, the display module 92 determines whether a view of the image has been saved using the Remember icon and retrieves it. If no view has been saved using the Remember icon, the original view is retrieved. While this is occurring, an animation display window appears on the screen 36a. The display window allows the user to select the number of intermediate views of the displayed image which are to be computed and displayed (see FIG. 14). The animation display window also allows the user to adjust the image size, assign an identifier to the animation sequence and preview the animation to ensure that the selected parameters are satisfactory. After this, the display module 92 computes the view orientation, position and orientation of each plane of the intermediate views by simultaneous interpolation between the saved the current views.

By using simultaneous interpolation, the user need only enter two views making the use of the feature very simple. Secondly it allows complicated view sequences to be produced which cannot be produced manually. When altering an image manually, a plane may be either rotated or translated but not translated and rotated at the same time. Simultaneous interpolation of plane position and orientation makes it possible to produce an animated view sequence in which a plane is rotated and translated at the same time. As should be realized, this feature as described can only be implemented when the current and saved views have the same number of planes.

If the indicator icon is selected, the model is displayed with axis indicators to indicate standard directions of the image, such as front F, back B, left L etc. These symbols may be changed by the user to suit the application. For example, in ophthalmic imaging the symbols can represent the standard ocular axes, namely superior S, inferior I, nasal N and temporal T. These indicators float as the view of the displayed image changes. To avoid cluttering, it is preferred that axis indicators disappear when the current view orientation would place then behind the displayed model.

Figure 15A:
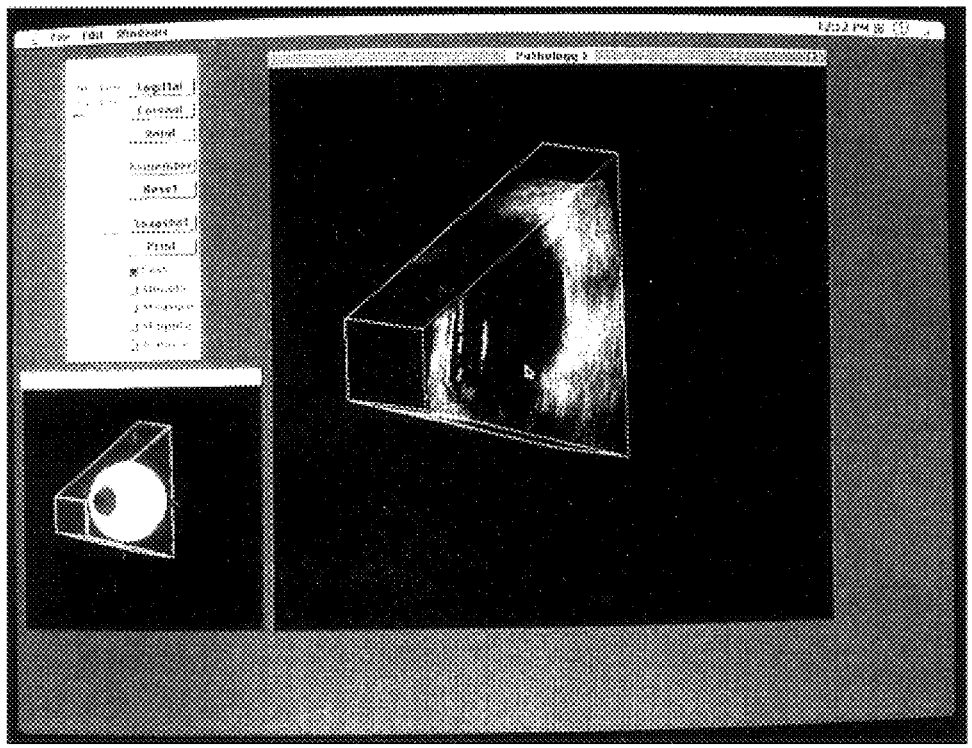
FIGS. 15a to 15c show full screen displays further including an orientation view window.
Figure 15B:
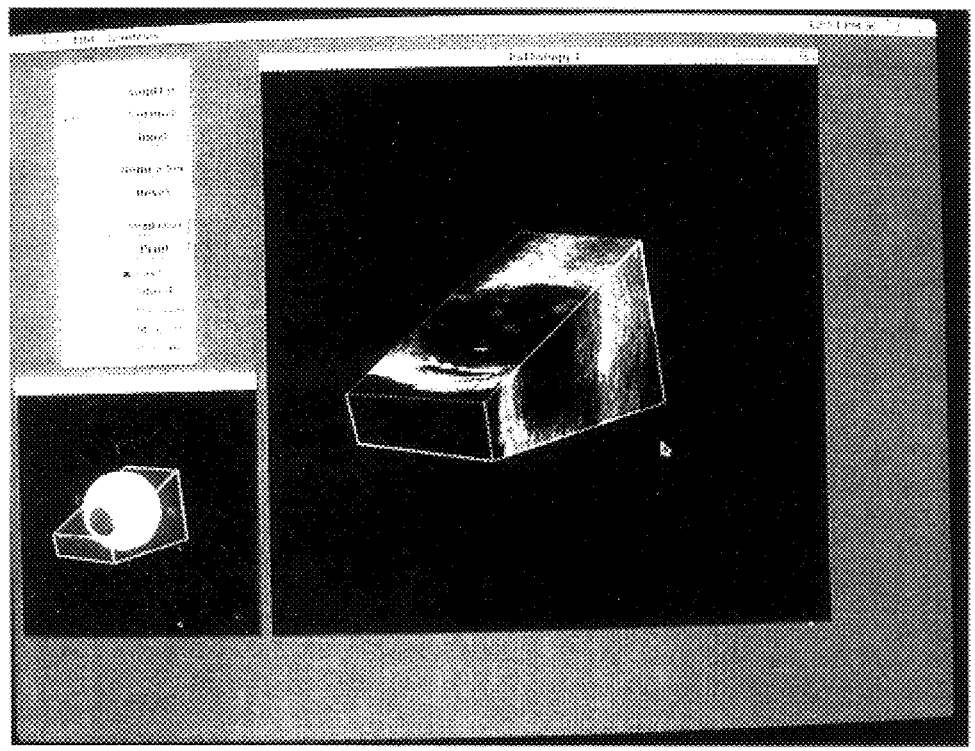
Figure 15C:
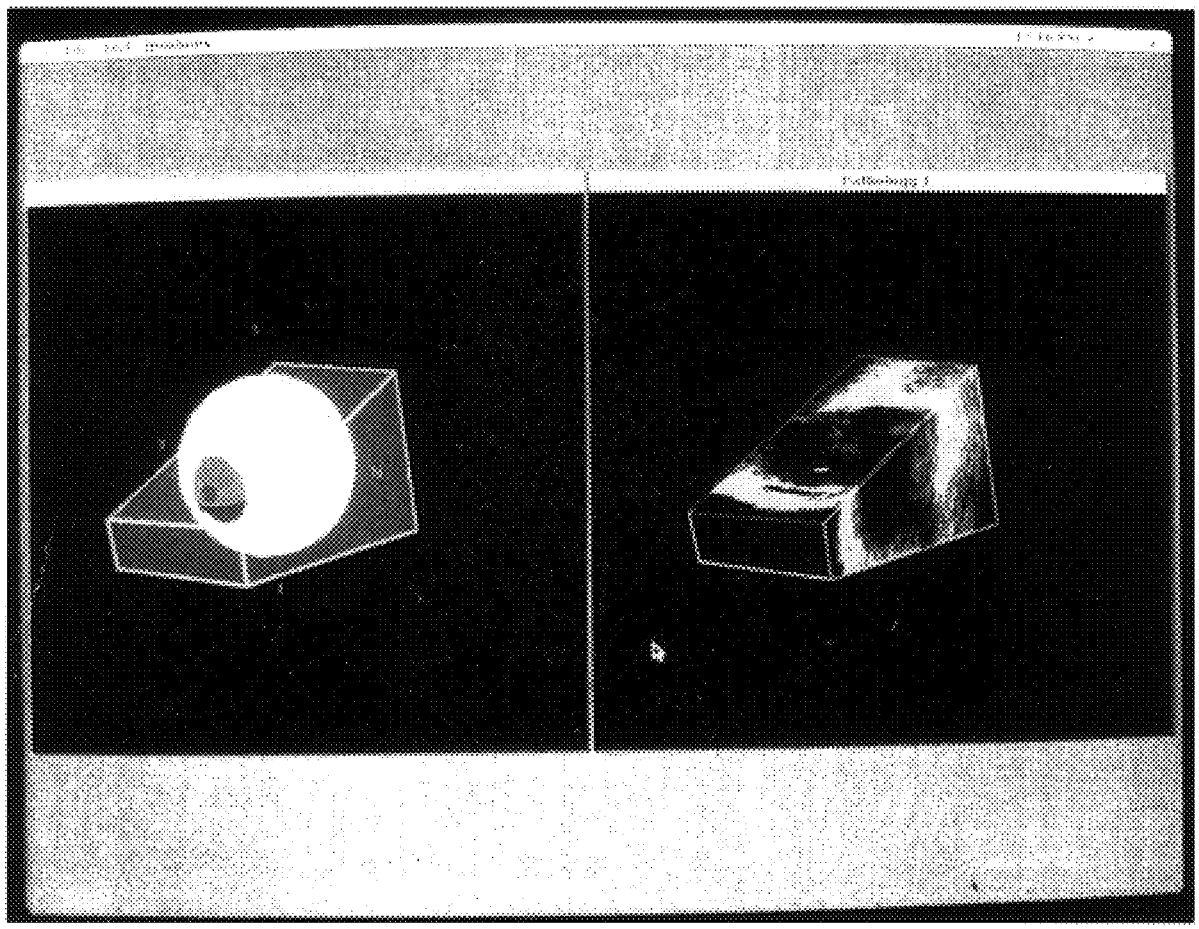

In some applications such as in medical imaging, it is desired to show the current spatial relationship of the model to a representation of the structure which has been imaged. This can be achieved when the Orientation icon is selected. When this icon is selected, the representation of the structure being imaged is selected from a list of stored structures. The structure is modelled using conventional three-dimensional computer graphics techniques. The structure is then displayed as a semi-transparent solid object intersecting the model polyhedron, either in the main display window or in a second display window elsewhere on the monitor screen. This requires use of a rendering algorithm which makes it apparent how the structure and model polyhedron intersect. The position, size and spatial orientation of the structure relative to the model polyhedron, which may be expressed as a 4×4 transformation matrix, must be determined. When this icon is selected, the structure display window is updated as the user manipulates the displayed view, so that the two displays are always oriented in the same manner. When computer power is limited, it is permissible to update the structure display less frequently then the main display window, e.g. to suppress updating the former until there is a pause in user input. This approach, which works best when the structure is displayed in a window distinct from the main window, is used in the present embodiment. FIGS. 15a to 15c show the model and three-dimensional image within the main window display as well as the structure of an eye in a second display window beside the main window display. As can be seen, in FIGS. 15a to 15b, the second display window is small and is positioned below the control display window while in FIG. 15c, the second display window has been increased in size.

The Fast and Smooth icons may be individually selected or deselected to enable or disable the first and third rendering passes described previously (the second pass is always enabled). The initial state of these icons is established during initialization at block 324. It should be realized that this general scheme can be altered slightly, e.g. by addition of a fourth pass with a corresponding option icon to selectively enable or disable it if desired.

Each displayed point of the image array $V(x,y,z)$ is converted to a pixel brightness or color by pseudo-color mapping. The domain of the pseudo-color mapping is the range of values in the volumetric image array $V(x,y,z)$. The pseudo-color mapping can be adjusted by a user via the window and level slide controls (labelled "Win" and "Lev" in FIGS. 13 to 15) to allow the contrast, brightness etc. of the display to be enhanced. The terms "window" and "level" and their interpretation have become standardized in the medical imaging field. The present embodiment is consistent with established medical imaging practice in this regard.

When the Magnify icon is selected, a magnifying window appears superimposed upon the main display window and can be moved over the displayed view. Cross-hairs are located at the center of the window and can be positioned over a certain area of the displayed view. When the cross-hairs are at the appropriate location, the user can use the graphical input device to adjust the magnification of the area at which the cross-hairs are located.

Figure 14:
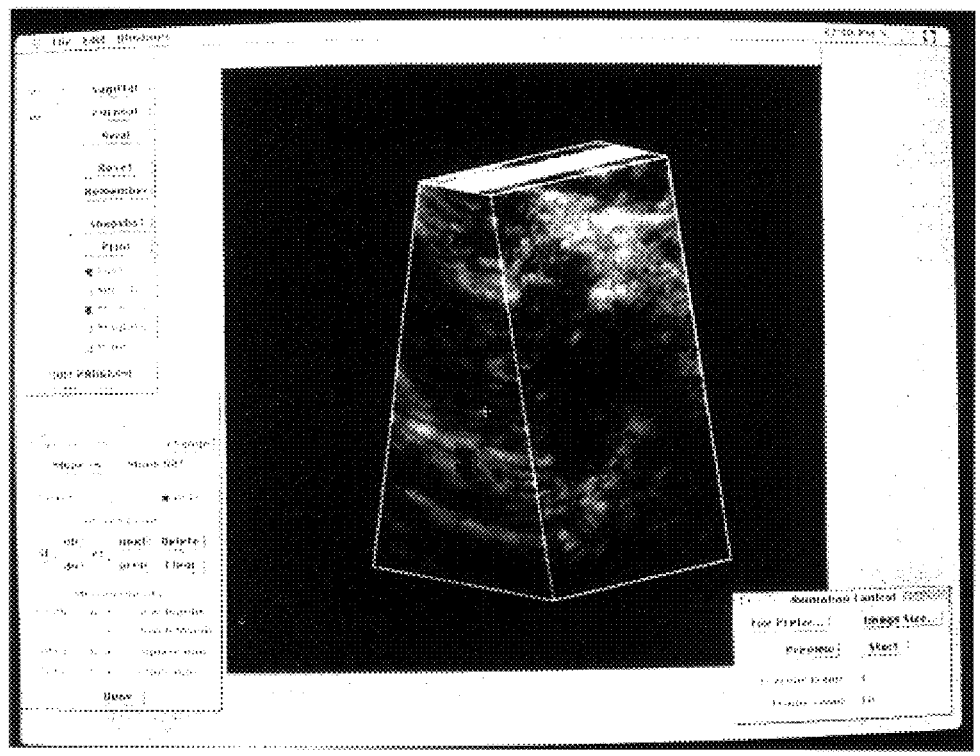
FIG. 14 shows another full screen display further including a measure control window and an animation control window.

When the Measure icon is selected, a measure display window appears on the screen (see FIG. 14). The user can use the graphical input device to measure distances and areas of the three-dimensional image within the most recently moved plane (i.e. The one denoted by yellow lines). If the user wishes to measure a distance, the user simply needs to use the graphical input device 38 to indicate the two end points over which the distance is to be measured. If an area is to be measured, the user must identify at least three points. When the cursor is moved over the most recently moved plane, it changes to cross-hairs to facilitate placement of the points on the image. The display module 92 in this mode connects adjacent points by straight line segments and computes both the overall line length and the area bounded by the lines joining the points using an appropriate scale.

If it is desired to change the drag sensitivity, the user can depress a specified key on the keyboard and this will adjust the scaling factor for as long as the key is depressed. This allows for greater or smaller mouse movements for a given change in the displayed image. This of course can also be achieved by increasing or decreasing the size of the main display window.

Although the animation function has been described to animate a sequence of translated and/or rotated images, the cine loop technique may also be applied to visualize four dimensional image arrays. In this case, the four-dimensional image arrays are a series of three-dimensional images of the same target volume, acquired at different times. For example in trans-oesophageal cardiac ultrasound imaging, it is possible to capture the reconstruct a plurality of images of the beating heart, each corresponding to a different point in the cardiac cycle. The three-dimensional images will all have the same spatial interpretation and hence, it is possible to impose a single bounding model upon all of them simultaneously. The intersection of the model polyhedron with each volume image yields a two-dimensional image. The images can be computed and displayed in time order as a cine loop.

Although the system has been described as including a single button mouse to allow a user to input commands, it should be apparent to those of skill in the art that other input/output devices such as a multi-button mouse, a digitizer, a light pen, a trackball, a keyboard or the like or any combination of the above an be used. When other input/output devices are used, different inputs can be chosen to represent different commands or to select the various icons.

When a graphical input device other than the single button mouse is used, manipulation of an image by rotation of a plane of the model can be enhanced. For example, if a mouse is used in combination with a keyboard and a keyboard input is used to signify that it is desired to rotate a plane, the fixed point of rotation of the plane can be determined by the position of the mouse when it is clicked and the keyboard input signifying rotation of the plane is selected. This allows the plane to be rotated about a point different from the geometric center of the initial model.

If a two button mouse is used as the input/output device, one of the buttons can be assigned to signify translation of a plane and the other button can be used to signify rotation of a plane. This avoids the need to examine the position of the cursor to determine whether it is within interior or exterior areas of the selected model face.

Although the three-dimensional image display technique has been described in an ultrasound three-dimensional imaging system, it should be apparent that the image display technique may be used in different environments where a three-dimensional image needs to be manipulated to allow different views of the image to be visualized. Specifically, the present display technique can be used to display any volumetric image array $V(x,y,z)$ which represents a discretely sampled function defined over a three-dimensional space. This allows the display technique to be used in other environments such as, for example, magnetic resonance imaging (MRI) and x-ray computed tomography (CT).

Although the system 20 has been described as including a clinical ultrasound machine 28 and a computer 32, it is contemplated that a single machine be used to perform the functions of both of these components.

Variations and modifications of the present invention should be apparent to those of skill in the art without departing from the scope of the present invention as defined by the dependant claims.

We claim:

1. A three-dimensional ultrasound imaging system for use with a transducer and a display, comprising:

an input for inputting ultrasound signals from the transducer; and a processor for (i) receiving the ultrasound signals input by said input, (ii) causing the storage of the received ultrasound signals as a plurality of two-dimensional image data, (iii) causing the stored two-dimensional image data to be assigned to at least one display model, (iv) causing a perimeter of the at least one assigned display model to be displayed on the display, (v) causing the display to display an image corresponding to a portion of the stored two-dimensional image data on a visible image face of the model perimeter, (vi) determining a depth value associated with pixels of the image displayed on the visible image face, and (vii) causing the storage of the determined depth values with their associated pixels as three-dimensional image data.

* * * * *